US012640257B2

(12) United States Patent　　　(10) Patent No.: US 12,640,257 B2
Dunstan et al.　　　　　　　　　(45) Date of Patent: ***May 26, 2026

(54) SENIOR LIVING CARE COORDINATION PLATFORMS

(71) Applicant: State Farm Mutual Automobile Insurance Company, Bloomington, IL (US)

(72) Inventors: Stephen Dunstan, Mountain View, CA (US); Vallory Clardy, Fremont, CA (US); Francesco Radicati, Palo Alto, CA (US); Matthew Morrison, Santa Clara, CA (US); Nirav Patel, Santa Clara, CA (US); Mary Kay Mueller, Normal, IL (US)

(73) Assignee: State Farm Mutual Automobile Insurance Company, Bloomington, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 18/492,405

(22) Filed: Oct. 23, 2023

(65) Prior Publication Data

US 2024/0047056 A1　　Feb. 8, 2024

Related U.S. Application Data

(63) Continuation of application No. 16/913,937, filed on Jun. 26, 2020, now Pat. No. 11,894,129.

(Continued)

(51) Int. Cl.
*G16H 40/20*　　　　(2018.01)
*A61B 5/00*　　　　(2006.01)
(Continued)

(52) U.S. Cl.
CPC ............ *G16H 40/20* (2018.01); *A61B 5/1118* (2013.01); *A61B 5/4833* (2013.01); *A61B 5/742* (2013.01);
(Continued)

(58) Field of Classification Search
CPC ........ G16H 15/00; G16H 40/20; G16H 50/20; G16H 20/30; G16H 20/10
(Continued)

(56) References Cited

U.S. PATENT DOCUMENTS 1,446,000 A　　2/1923　Cleland
5,553,609 A　　9/1996　Chen
(Continued)

FOREIGN PATENT DOCUMENTS

CA　　　　2781251 A1　　12/2013
IN　　201811043670 A　　7/2018
(Continued)

OTHER PUBLICATIONS

Easton, Katherine et al.; A Virtual Agent to Support Individuals Living With Physical and Mental Comorbidities: Co-Design and Acceptability Testing; J Med Internet Res. May 30, 2019;21(5):e12996 (Year: 2019).*

(Continued)

*Primary Examiner* — Hiep V Nguyen
(74) *Attorney, Agent, or Firm* — Armstrong Teasdale LLP

(57) ABSTRACT

Provided herein is a care coordination support platform ("CCSP") computer system including a in communication with a memory device for coordinating care. The processor is programmed to: (i) register a user through an application, (ii) register a caregiver through the application, (iii) receive input from the user or the caregiver defining an event of the user, (iv) assign the event to a caregiver based upon personal and scheduling data of the caregivers, (v) create a care (Continued)

schedule of the user, (vi) display the care schedule to the caregiver, (vii) receive a question regarding the from the user or the caregiver, (viii) convert the question into a query, (ix) run the query against an event database, and (x) transmit a response to the question to the processor.

21 Claims, 14 Drawing Sheets

Related U.S. Application Data

(60) Provisional application No. 62/874,258, filed on Jul. 15, 2019, provisional application No. 62/872,014, filed on Jul. 9, 2019, provisional application No. 62/870,515, filed on Jul. 3, 2019.

(51) Int. Cl.

| | |
|---|---|
| *A61B 5/11* | (2006.01) |
| *G06F 16/2452* | (2019.01) |
| *G06Q 10/0631* | (2023.01) |
| *G06Q 10/109* | (2023.01) |
| *G06Q 10/1091* | (2023.01) |
| *G06Q 10/1093* | (2023.01) |
| *G06Q 10/20* | (2023.01) |
| *G06Q 10/40* | (2026.01) |
| *G10L 15/18* | (2013.01) |
| *G10L 15/22* | (2006.01) |
| *G10L 15/30* | (2013.01) |
| *G16H 10/20* | (2018.01) |
| *G16H 15/00* | (2018.01) |
| *G16H 20/10* | (2018.01) |
| *G16H 20/30* | (2018.01) |
| *G16H 20/60* | (2018.01) |
| *G16H 40/67* | (2018.01) |
| *G16H 50/20* | (2018.01) |
| *H04L 51/02* | (2022.01) |
| *H04L 67/55* | (2022.01) |
| *G06Q 30/0207* | (2023.01) |

(52) U.S. Cl.
CPC ............ *A61B 5/746* (2013.01); *A61B 5/7465* (2013.01); *G06F 16/24522* (2019.01); *G06Q 10/06311* (2013.01); *G06Q 10/06312* (2013.01); *G06Q 10/06314* (2013.01); *G06Q 10/1091* (2013.01); *G06Q 10/1093* (2013.01); *G06Q 10/1097* (2013.01); *G06Q 10/20* (2013.01); *G06Q 10/40* (2026.01); *G10L 15/18* (2013.01); *G10L 15/22* (2013.01); *G10L 15/30* (2013.01); *G16H 10/20* (2018.01); *G16H 15/00* (2018.01); *G16H 20/10* (2018.01); *G16H 20/30* (2018.01); *G16H 20/60* (2018.01); *G16H 40/67* (2018.01); *G16H 50/20* (2018.01); *H04L 51/02* (2013.01); *H04L 67/55* (2022.05); *G06Q 30/0215* (2013.01); *G06Q 30/0236* (2013.01); *G10L 2015/223* (2013.01)

(58) Field of Classification Search
USPC .......................................................... 705/2
See application file for complete search history.

(56) References Cited

U.S. PATENT DOCUMENTS

| | | | |
|---|---|---|---|
| 5,703,995 | A | 12/1997 | Willbanks |
| 5,935,251 | A | 8/1999 | Moore |
| 5,967,975 | A | 10/1999 | Ridgeway |
| 6,428,475 | B1 | 8/2002 | Shen |
| 6,611,206 | B2 | 8/2003 | Eshelman |
| 6,847,892 | B2 | 1/2005 | Zhou |
| 6,886,139 | B2 | 4/2005 | Liu |
| 7,091,865 | B2 | 8/2006 | Cuddihy |
| 7,154,399 | B2 | 12/2006 | Cuddihy |
| 7,242,305 | B2 | 7/2007 | Cuddihy |
| 7,289,965 | B1 | 10/2007 | Bradley et al. |
| 7,301,463 | B1 | 11/2007 | Paterno |
| 7,397,346 | B2 | 7/2008 | Helal |
| 7,411,510 | B1 | 8/2008 | Nixon |
| 7,498,985 | B1 | 3/2009 | Woo |
| 7,502,498 | B2 | 3/2009 | Wen |
| 7,562,121 | B2 | 7/2009 | Berisford |
| 7,586,418 | B2 | 9/2009 | Cuddihy |
| 7,733,224 | B2 | 6/2010 | Tran |
| 7,801,612 | B2 | 9/2010 | Johnson |
| 7,831,235 | B2 | 11/2010 | Mononen |
| 7,835,926 | B1 | 11/2010 | Naidoo |
| 7,865,386 | B2 | 1/2011 | Sarkar |
| 7,911,334 | B2 | 3/2011 | Busey |
| 7,966,378 | B2 | 6/2011 | Berisford |
| 8,019,622 | B2 | 9/2011 | Kaboff |
| 8,050,665 | B1 | 11/2011 | Orbach |
| 8,131,875 | B1 | 3/2012 | Chen et al. |
| 8,214,082 | B2 | 7/2012 | Tsai |
| 8,346,594 | B2 | 1/2013 | Begeja |
| 8,490,006 | B1 | 7/2013 | Reeser |
| 8,527,306 | B1 | 9/2013 | Reeser |
| 8,529,456 | B2 | 9/2013 | Cobain |
| 8,533,144 | B1 | 9/2013 | Reeser |
| 8,589,806 | B1 | 11/2013 | Sena |
| 8,640,038 | B1 | 1/2014 | Reeser |
| 8,665,084 | B2 | 3/2014 | Shapiro |
| 8,669,864 | B1 | 3/2014 | Tedesco |
| 8,670,998 | B2 | 3/2014 | Bertha |
| 8,675,920 | B2 | 3/2014 | Hanson |
| 8,676,833 | B2 | 3/2014 | Chunilal |
| 8,682,952 | B2 | 3/2014 | Kutzik |
| 8,744,901 | B2 | 6/2014 | Begeja |
| 8,803,690 | B2 | 8/2014 | Junqua |
| 8,856,383 | B2 | 10/2014 | Beninato |
| 8,868,616 | B1 | 10/2014 | Otto |
| 8,882,666 | B1 | 11/2014 | Goldberg |
| 8,890,680 | B2 | 11/2014 | Reeser |
| 8,917,186 | B1 | 12/2014 | Grant |
| 8,929,853 | B2 | 1/2015 | Butler |
| 8,965,327 | B2 | 2/2015 | Davis |
| 8,976,937 | B2 | 3/2015 | Shapiro |
| 9,049,168 | B2 | 6/2015 | Jacob |
| 9,057,746 | B1 | 6/2015 | Houlette |
| 9,117,349 | B2 | 8/2015 | Shapiro |
| 9,142,119 | B1 | 9/2015 | Grant |
| 9,152,737 | B1 | 10/2015 | Micali |
| 9,165,334 | B2 | 10/2015 | Simon |
| 9,183,578 | B1 | 11/2015 | Reeser |
| 9,202,363 | B1 | 12/2015 | Grant |
| 9,208,661 | B2 | 12/2015 | Junqua |
| 9,262,909 | B1 | 2/2016 | Grant |
| 9,286,772 | B2 | 3/2016 | Shapiro |
| 9,344,330 | B2 | 5/2016 | Jacob |
| 9,349,300 | B2 | 5/2016 | Harkness |
| 9,375,142 | B2 | 6/2016 | Schultz |
| 9,408,561 | B2 | 8/2016 | Stone |
| 9,424,737 | B2 | 8/2016 | Bailey |
| 9,443,195 | B2 | 9/2016 | Micali |
| 9,472,092 | B1 | 10/2016 | Grant |
| 9,491,277 | B2 | 11/2016 | Vincent |
| 9,536,052 | B2 | 1/2017 | Amarasingham |
| 9,585,563 | B2 | 3/2017 | Mensinger et al. |
| 9,589,441 | B2 | 3/2017 | Shapiro |
| 9,609,003 | B1 | 3/2017 | Chmielewski |
| 9,665,892 | B1 | 5/2017 | Reeser |
| 9,666,060 | B2 | 5/2017 | Reeser |
| 9,699,529 | B1 | 7/2017 | Petri |
| 9,712,576 | B1 | 7/2017 | Gill |
| 9,739,813 | B2 | 8/2017 | Houlette |
| 9,754,477 | B2 | 9/2017 | Poder |
| 9,767,680 | B1 | 9/2017 | Trundle |

(56) References Cited

U.S. PATENT DOCUMENTS

| | | | |
|---|---|---|---|
| 9,786,158 B2 | 10/2017 | Beaver |
| 9,798,979 B2 | 10/2017 | Fadell |
| 9,798,993 B2 | 10/2017 | Payne |
| 9,800,570 B1 | 10/2017 | Bleisch |
| 9,800,958 B1 | 10/2017 | Petri |
| 9,801,541 B2 | 10/2017 | Mensinger |
| 9,812,001 B1 | 11/2017 | Grant |
| 9,838,854 B2 | 12/2017 | Fretwell |
| 9,866,507 B2 | 1/2018 | Frenkel |
| 9,888,371 B1 | 2/2018 | Jacob |
| 9,892,463 B1 | 2/2018 | Hakimi-Boushehri |
| 9,898,168 B2 | 2/2018 | Shapiro |
| 9,898,912 B1 | 2/2018 | Jordan, II |
| 9,901,252 B2 | 2/2018 | Tran |
| 9,911,042 B1 | 3/2018 | Cardona |
| 9,922,524 B2 | 3/2018 | Devdas |
| 9,923,971 B2 | 3/2018 | Madey |
| 9,936,076 B1 | 4/2018 | Tanner |
| 9,942,630 B1 | 4/2018 | Petri |
| 9,947,202 B1 | 4/2018 | Moon |
| 9,978,033 B1 | 5/2018 | Payne |
| 9,997,056 B2 | 6/2018 | Bleisch |
| 10,002,295 B1 | 6/2018 | Cardona |
| 10,022,084 B2 | 7/2018 | Nonaka |
| 10,042,341 B1 | 8/2018 | Jacob |
| 10,043,369 B2 | 8/2018 | Hopkins |
| 10,047,974 B1 | 8/2018 | Riblet |
| 10,055,793 B1 | 8/2018 | Call |
| 10,055,803 B2 | 8/2018 | Orduna |
| 10,057,664 B1 | 8/2018 | Moon |
| 10,073,929 B2 | 9/2018 | Vaynriber |
| 10,102,584 B1 | 10/2018 | Devereaux |
| 10,102,585 B1 | 10/2018 | Bryant |
| 10,107,708 B1 | 10/2018 | Schick |
| 10,136,294 B2 | 11/2018 | Mehta |
| 10,140,666 B1 | 11/2018 | Wang et al. |
| 10,142,394 B2 | 11/2018 | Chmielewski |
| 10,147,296 B2 | 12/2018 | Gregg |
| 10,152,150 B2 | 12/2018 | Sherman |
| 10,176,705 B1 | 1/2019 | Grant |
| 10,181,160 B1 | 1/2019 | Hakimi-Boushehri |
| 10,181,246 B1 | 1/2019 | Jackson |
| 10,186,134 B1 | 1/2019 | Moon |
| 10,198,771 B1 | 2/2019 | Madigan |
| 10,204,500 B2 | 2/2019 | Cullin |
| 10,206,630 B2 | 2/2019 | Stone |
| 10,217,068 B1 | 2/2019 | Davis |
| 10,226,187 B2 | 3/2019 | Al-Ali |
| 10,226,204 B2 | 3/2019 | Heaton |
| 10,229,394 B1 | 3/2019 | Davis |
| 10,244,294 B1 | 3/2019 | Moon |
| 10,249,158 B1 | 4/2019 | Jordan, II |
| 10,258,295 B2 | 4/2019 | Fountaine |
| 10,282,787 B1 | 5/2019 | Hakimi-Boushehri |
| 10,282,788 B1 | 5/2019 | Jordan, II |
| 10,282,961 B1 | 5/2019 | Jordan, II |
| 10,295,431 B1 | 5/2019 | Schick |
| 10,297,138 B2 | 5/2019 | Reeser |
| 10,298,735 B2 | 5/2019 | Preston |
| 10,304,311 B2 | 5/2019 | Clark |
| 10,304,313 B1 | 5/2019 | Moon |
| 10,319,209 B2 | 6/2019 | Carlton-Foss |
| 10,323,860 B1 | 6/2019 | Riblet |
| 10,325,471 B1 | 6/2019 | Victor |
| 10,325,473 B1 | 6/2019 | Moon |
| 10,332,059 B2 | 6/2019 | Matsuoka |
| 10,335,059 B2 | 7/2019 | Annegarn |
| 10,346,811 B1 | 7/2019 | Jordan, II |
| 10,353,359 B1 | 7/2019 | Jordan, II |
| 10,356,303 B1 | 7/2019 | Jordan, II |
| 10,360,345 B2 | 7/2019 | Ramsdell |
| 10,373,257 B1 | 8/2019 | Iqbal et al. |
| 10,380,692 B1 | 8/2019 | Parker |
| 10,387,966 B1 | 8/2019 | Shah |
| 10,388,135 B1 | 8/2019 | Jordan, II |
| 10,412,169 B1 | 9/2019 | Madey |
| 10,446,000 B2 | 10/2019 | Friar |
| 10,446,007 B2 | 10/2019 | Kawazu |
| 10,467,476 B1 | 11/2019 | Cardona |
| 10,475,141 B2 | 11/2019 | Mcintosh |
| 10,480,825 B1 | 11/2019 | Riblet |
| 10,482,746 B1 | 11/2019 | Moon |
| 10,506,411 B1 | 12/2019 | Jacob |
| 10,506,990 B2 | 12/2019 | Lee |
| 10,514,669 B1 | 12/2019 | Call |
| 10,515,372 B1 | 12/2019 | Jordan, II |
| 10,522,009 B1 | 12/2019 | Jordan, II |
| 10,522,021 B1 | 12/2019 | Victor |
| 10,546,478 B1 | 1/2020 | Moon |
| 10,547,918 B1 | 1/2020 | Moon |
| 10,548,512 B2 | 2/2020 | Hausdorff |
| 10,565,541 B2 | 2/2020 | Payne |
| 10,573,146 B1 | 2/2020 | Jordan, II |
| 10,573,149 B1 | 2/2020 | Jordan, II |
| 10,579,028 B1 | 3/2020 | Jacob |
| 10,586,177 B1 | 3/2020 | Choueiter |
| 10,607,295 B1 | 3/2020 | Hakimi-Boushehri |
| 10,621,686 B2 | 4/2020 | Mazar |
| 10,623,790 B2 | 4/2020 | Maddalena |
| 10,634,576 B1 | 4/2020 | Schick |
| 10,679,292 B1 | 6/2020 | Call |
| 10,685,402 B1 | 6/2020 | Bryant |
| 10,726,494 B1 | 7/2020 | Shah |
| 10,726,500 B1 | 7/2020 | Shah |
| 10,733,671 B1 | 8/2020 | Hakimi-Boushehri |
| 10,733,868 B2 | 8/2020 | Moon |
| 10,735,829 B2 | 8/2020 | Petri |
| 10,740,691 B2 | 8/2020 | Choueiter |
| 10,741,033 B1 | 8/2020 | Jordan, II |
| 10,750,252 B2 | 8/2020 | Petri |
| 10,795,329 B1 | 10/2020 | Jordan, II |
| 10,796,557 B2 | 10/2020 | Sundermeyer |
| 10,810,574 B1 | 10/2020 | Wilson et al. |
| 10,823,458 B1 | 11/2020 | Riblet |
| 10,824,971 B1 | 11/2020 | Davis |
| 10,825,318 B1 | 11/2020 | Williams |
| 10,825,320 B1 | 11/2020 | Moon |
| 10,825,321 B2 | 11/2020 | Moon |
| 10,832,225 B1 | 11/2020 | Davis |
| 10,846,800 B1 | 11/2020 | Bryant |
| 10,878,062 B1 | 12/2020 | Garavaglia et al. |
| 10,922,756 B1 | 2/2021 | Call |
| 10,922,948 B1 | 2/2021 | Moon |
| 10,943,447 B1 | 3/2021 | Jordan, II |
| 10,970,990 B1 | 4/2021 | Jacob |
| 10,990,069 B1 | 4/2021 | Jacob |
| 11,004,320 B1 | 5/2021 | Jordan, II |
| 11,015,997 B1 | 5/2021 | Schick |
| 11,017,480 B2 | 5/2021 | Shah |
| 11,024,142 B2 | 6/2021 | Tunnell |
| 11,042,137 B1 | 6/2021 | Call |
| 11,042,942 B1 | 6/2021 | Hakimi-Boushehri |
| 11,043,098 B1 | 6/2021 | Jordan, II |
| 11,049,078 B1 | 6/2021 | Jordan, II |
| 11,049,189 B2 | 6/2021 | Shah |
| 11,070,644 B1 | 7/2021 | Da Teng et al. |
| 11,074,659 B1 | 7/2021 | Hakimi-Boushehri |
| 11,094,180 B1 | 8/2021 | Williams |
| 11,107,465 B2 | 8/2021 | Gustman et al. |
| 11,118,812 B1 | 9/2021 | Riblet |
| 11,120,226 B1 | 9/2021 | Nudd |
| 11,126,708 B2 | 9/2021 | Reimer |
| 11,188,840 B1 | 11/2021 | Rivera et al. |
| 11,301,502 B1 | 4/2022 | Dijamco et al. |
| 11,394,799 B2 | 7/2022 | Jackson |
| 11,431,660 B1 | 8/2022 | Leeds et al. |
| 11,436,549 B1 | 9/2022 | Hull et al. |
| 11,581,099 B1 | 2/2023 | Rufo et al. |
| 11,587,555 B1 | 2/2023 | Pathak |
| 11,853,919 B1 | 12/2023 | Mangat et al. |
| 2002/0046047 A1 | 4/2002 | Budd |
| 2002/0116256 A1 | 8/2002 | de Rafael et al. |
| 2002/0169631 A1 | 11/2002 | Lewis |
| 2002/0194048 A1 | 12/2002 | Levinson |

(56) References Cited

U.S. PATENT DOCUMENTS

| | | |
|---|---|---|
| 2003/0001742 A1 | 1/2003 | Eshelman |
| 2003/0023459 A1 | 1/2003 | Shipon |
| 2003/0144793 A1 | 7/2003 | Melaku |
| 2004/0030531 A1 | 2/2004 | Miller |
| 2004/0078220 A1 | 4/2004 | Jackson |
| 2004/0220538 A1 | 11/2004 | Panopoulos |
| 2004/0249250 A1 | 12/2004 | McGee |
| 2005/0137465 A1 | 6/2005 | Cuddihy |
| 2005/0142524 A1 | 6/2005 | Simon |
| 2005/0174242 A1 | 8/2005 | Cohen |
| 2005/0228245 A1 | 10/2005 | Quy |
| 2006/0143060 A1 | 6/2006 | Conry |
| 2006/0205564 A1 | 9/2006 | Peterson |
| 2006/0293924 A1 | 12/2006 | Gardiner |
| 2007/0186165 A1 | 8/2007 | Maislos |
| 2007/0214002 A1 | 9/2007 | Smith |
| 2007/0250791 A1 | 10/2007 | Halliday et al. |
| 2007/0274464 A1* | 11/2007 | Cameron ............... G06Q 30/00 |
| | | 379/38 |
| 2007/0282476 A1 | 12/2007 | Song |
| 2008/0084296 A1 | 4/2008 | Kutzik |
| 2008/0154099 A1 | 6/2008 | Aspel |
| 2008/0201174 A1 | 8/2008 | Ramasubramanian |
| 2008/0235629 A1 | 9/2008 | Porter |
| 2008/0240379 A1 | 10/2008 | Maislos |
| 2008/0292151 A1 | 11/2008 | Kurtz |
| 2008/0294462 A1 | 11/2008 | Nuhaan |
| 2008/0294490 A1 | 11/2008 | Nuhaan |
| 2009/0010106 A1 | 1/2009 | Levy |
| 2009/0012373 A1 | 1/2009 | Raij |
| 2009/0048865 A1 | 2/2009 | Breazeale, Jr. |
| 2009/0259492 A1 | 10/2009 | Cossman |
| 2009/0265185 A1 | 10/2009 | Finn |
| 2009/0265193 A1 | 10/2009 | Collins |
| 2009/0281393 A1 | 11/2009 | Smith |
| 2009/0315735 A1 | 12/2009 | Bhavani |
| 2009/0326981 A1 | 12/2009 | Karkanias |
| 2010/0017718 A1 | 1/2010 | Bohms |
| 2010/0145164 A1 | 6/2010 | Howell |
| 2010/0191824 A1 | 7/2010 | Lindsay |
| 2010/0198608 A1 | 8/2010 | Kaboff |
| 2010/0217619 A1* | 8/2010 | Cox ....................... G16H 80/00 |
| | | 715/757 |
| 2010/0222649 A1 | 9/2010 | Schoenberg |
| 2010/0286490 A1 | 11/2010 | Koverzin |
| 2010/0306824 A1 | 12/2010 | Gurney et al. |
| 2011/0021140 A1 | 1/2011 | Binier |
| 2011/0092779 A1 | 4/2011 | Chang et al. |
| 2011/0125844 A1 | 5/2011 | Collier |
| 2011/0181422 A1 | 7/2011 | Tran |
| 2011/0201901 A1 | 8/2011 | Khanuja |
| 2011/0202345 A1 | 8/2011 | Meyer et al. |
| 2011/0224501 A1 | 9/2011 | Hudsmith |
| 2011/0246123 A1 | 10/2011 | DelloStritto |
| 2012/0095846 A1 | 4/2012 | Leverant |
| 2012/0143619 A1 | 6/2012 | Routt |
| 2012/0191788 A1 | 7/2012 | Mellen |
| 2012/0197662 A1 | 8/2012 | Sun et al. |
| 2012/0254021 A1 | 10/2012 | Wohied et al. |
| 2012/0280811 A1 | 11/2012 | McKalip |
| 2012/0284040 A1 | 11/2012 | Dupin |
| 2012/0284637 A1 | 11/2012 | Boyer et al. |
| 2013/0035946 A1 | 2/2013 | Ratan et al. |
| 2013/0065569 A1 | 3/2013 | Leipzig |
| 2013/0073299 A1 | 3/2013 | Warman |
| 2013/0073306 A1 | 3/2013 | Shlain |
| 2013/0080209 A1 | 3/2013 | Begeja |
| 2013/0082842 A1 | 4/2013 | Balazs |
| 2013/0095459 A1 | 4/2013 | Tran |
| 2013/0100268 A1 | 4/2013 | Mihailidis |
| 2013/0110895 A1 | 5/2013 | Valentino et al. |
| 2013/0147899 A1 | 6/2013 | Labhard |
| 2013/0148942 A1 | 6/2013 | Ryan et al. |
| 2013/0191140 A1 | 7/2013 | Fotheringham et al. |
| 2013/0226578 A1 | 8/2013 | Bolton et al. |
| 2013/0262155 A1 | 10/2013 | HinKamp |
| 2013/0267795 A1 | 10/2013 | Cosentino |
| 2013/0297350 A1 | 11/2013 | Gross et al. |
| 2013/0332959 A1 | 12/2013 | Kothari |
| 2014/0052474 A1 | 2/2014 | Madan |
| 2014/0074454 A1* | 3/2014 | Brown ..................... G10L 15/08 |
| | | 704/235 |
| 2014/0108031 A1 | 4/2014 | Ferrara |
| 2014/0129160 A1 | 5/2014 | Tran |
| 2014/0136264 A1 | 5/2014 | Kinsey, II |
| 2014/0148733 A1 | 5/2014 | Stone |
| 2014/0188997 A1 | 7/2014 | Schneiderman et al. |
| 2014/0207486 A1 | 7/2014 | Carty |
| 2014/0207492 A1 | 7/2014 | Farooq et al. |
| 2014/0257851 A1 | 9/2014 | Walker |
| 2014/0266669 A1 | 9/2014 | Fadell |
| 2014/0266791 A1 | 9/2014 | Lloyd |
| 2014/0282828 A1 | 9/2014 | Stuntebeck |
| 2014/0284348 A1 | 9/2014 | Cheng |
| 2014/0324757 A1 | 10/2014 | Tabrizi et al. |
| 2014/0362213 A1 | 12/2014 | Tseng |
| 2015/0002293 A1 | 1/2015 | Nepo |
| 2015/0006200 A1 | 1/2015 | Chaput |
| 2015/0020170 A1 | 1/2015 | Talley |
| 2015/0077237 A1 | 3/2015 | Chou |
| 2015/0094144 A1 | 4/2015 | Brown et al. |
| 2015/0094830 A1 | 4/2015 | Lipoma |
| 2015/0134343 A1 | 5/2015 | Kluger |
| 2015/0154880 A1 | 6/2015 | Petito |
| 2015/0179040 A1 | 6/2015 | Nishihara |
| 2015/0194032 A1 | 7/2015 | Wright |
| 2015/0213224 A1 | 7/2015 | Amarasingham |
| 2015/0223705 A1 | 8/2015 | Sadhu |
| 2015/0254412 A1 | 9/2015 | Humphrys et al. |
| 2015/0269329 A1 | 9/2015 | Fearon |
| 2015/0288797 A1 | 10/2015 | Vincent |
| 2015/0302331 A1 | 10/2015 | Randall |
| 2015/0302538 A1 | 10/2015 | Mazar |
| 2015/0312740 A1 | 10/2015 | Li |
| 2015/0356701 A1 | 12/2015 | Gandy |
| 2016/0026354 A1 | 1/2016 | Mcintosh |
| 2016/0027278 A1 | 1/2016 | Mcintosh |
| 2016/0086255 A1 | 3/2016 | Sainfort |
| 2016/0106627 A1 | 4/2016 | Geman et al. |
| 2016/0110509 A1 | 4/2016 | Girardeau |
| 2016/0140320 A1 | 5/2016 | Moturu |
| 2016/0155163 A1 | 6/2016 | White |
| 2016/0162785 A1 | 6/2016 | Grobman |
| 2016/0171864 A1 | 6/2016 | Ciaramelletti |
| 2016/0174913 A1 | 6/2016 | Somanath |
| 2016/0203444 A1 | 7/2016 | Frank et al. |
| 2016/0210427 A1 | 7/2016 | Mynhier |
| 2016/0210434 A1 | 7/2016 | Al-Sharif |
| 2016/0214571 A1 | 7/2016 | Othmer et al. |
| 2016/0225240 A1 | 8/2016 | Voddhi |
| 2016/0246936 A1 | 8/2016 | Kahn |
| 2016/0259902 A1 | 9/2016 | Feldman |
| 2016/0275475 A1 | 9/2016 | Lin et al. |
| 2016/0292373 A1 | 10/2016 | Spors et al. |
| 2016/0314514 A1 | 10/2016 | High |
| 2016/0342767 A1 | 11/2016 | Narasimhan |
| 2016/0350721 A1 | 12/2016 | Comerford |
| 2016/0371620 A1* | 12/2016 | Nascenzi ......... G06Q 10/06314 |
| 2017/0004273 A1 | 1/2017 | Mbanefo |
| 2017/0004463 A1 | 1/2017 | Stroeh et al. |
| 2017/0004695 A1 | 1/2017 | Brasch |
| 2017/0011188 A1 | 1/2017 | Arshad |
| 2017/0011195 A1 | 1/2017 | Arshad |
| 2017/0024525 A1 | 1/2017 | Walker |
| 2017/0046501 A1 | 2/2017 | Coleman |
| 2017/0094057 A1 | 3/2017 | Naiga et al. |
| 2017/0116384 A1 | 4/2017 | Ghani |
| 2017/0124276 A1 | 5/2017 | Tee |
| 2017/0124277 A1 | 5/2017 | Shlagman |
| 2017/0124526 A1* | 5/2017 | Sanderford ........ G06Q 10/1095 |
| 2017/0140486 A1 | 5/2017 | Neha et al. |
| 2017/0193164 A1 | 7/2017 | Simon |
| 2017/0214758 A1 | 7/2017 | Engel |
| 2017/0221336 A1 | 8/2017 | Ogaz |

(56) References Cited

U.S. PATENT DOCUMENTS

| 2017/0228109 A1 | 8/2017 | Zhang |
| 2017/0242886 A1 | 8/2017 | Jolley et al. |
| 2017/0262604 A1 | 9/2017 | Francois |
| 2017/0270260 A1 | 9/2017 | Shetty |
| 2017/0277834 A1 | 9/2017 | Zipnick |
| 2017/0293878 A1 | 10/2017 | Donnelly |
| 2017/0300626 A1 | 10/2017 | Love |
| 2018/0007131 A1 | 1/2018 | Cohn |
| 2018/0032696 A1 | 2/2018 | Rome |
| 2018/0060970 A1 | 3/2018 | Oduor et al. |
| 2018/0068081 A1 | 3/2018 | Salem |
| 2018/0075204 A1 | 3/2018 | Lee |
| 2018/0082184 A1 | 3/2018 | Guo |
| 2018/0153477 A1 | 6/2018 | Nagale |
| 2018/0158080 A1 | 6/2018 | Mehl |
| 2018/0158548 A1 | 6/2018 | Taheri |
| 2018/0177436 A1 | 6/2018 | Chang |
| 2018/0182055 A1 | 6/2018 | Jepson |
| 2018/0194919 A1 | 7/2018 | Wu |
| 2018/0196919 A1 | 7/2018 | Abou Mahmoud |
| 2018/0209806 A1 | 7/2018 | Rakah et al. |
| 2018/0211509 A1 | 7/2018 | Ramaci |
| 2018/0211724 A1 | 7/2018 | Wang |
| 2018/0225649 A1 | 8/2018 | Babar et al. |
| 2018/0255114 A1 | 9/2018 | Dharmaji |
| 2018/0260384 A1 | 9/2018 | Pasupalak et al. |
| 2018/0276710 A1 | 9/2018 | Tietzen |
| 2018/0280245 A1 | 10/2018 | Khalid |
| 2018/0308569 A1 | 10/2018 | Luellen |
| 2018/0315499 A1 | 11/2018 | Appelbaum |
| 2018/0322469 A1 | 11/2018 | Logtenberg |
| 2018/0322947 A1 | 11/2018 | Potts |
| 2018/0325470 A1 | 11/2018 | Fountaine |
| 2018/0336048 A1 | 11/2018 | Zarlengo et al. |
| 2018/0342329 A1 | 11/2018 | Rufo |
| 2018/0344215 A1 | 12/2018 | Ohnemus |
| 2018/0357386 A1 | 12/2018 | Sanjay-Gopal |
| 2018/0365957 A1 | 12/2018 | Wright |
| 2019/0028758 A1 | 1/2019 | Talvensaari et al. |
| 2019/0046039 A1 | 2/2019 | Ramesh |
| 2019/0069154 A1 | 2/2019 | Booth |
| 2019/0080056 A1 | 3/2019 | Das |
| 2019/0083003 A1 | 3/2019 | Lee |
| 2019/0095540 A1 | 3/2019 | Antao et al. |
| 2019/0108841 A1 | 4/2019 | Vergyri |
| 2019/0122522 A1 | 4/2019 | Stefanski |
| 2019/0122760 A1 | 4/2019 | Wang |
| 2019/0133445 A1 | 5/2019 | Eteminan |
| 2019/0156944 A1 | 5/2019 | Eriksson |
| 2019/0180868 A1 | 6/2019 | Makram |
| 2019/0182299 A1 | 6/2019 | O'Brien |
| 2019/0198169 A1 | 6/2019 | T |
| 2019/0205675 A1 | 7/2019 | McGill |
| 2019/0206533 A1 | 7/2019 | Singh |
| 2019/0213557 A1 | 7/2019 | Dotan-Cohen et al. |
| 2019/0228657 A1 | 7/2019 | O'Sullivan |
| 2019/0267133 A1 | 8/2019 | Schwarz et al. |
| 2019/0279116 A1 | 9/2019 | Caligor |
| 2019/0279647 A1 * | 9/2019 | Jones ..................... G16H 10/60 |
| 2019/0281327 A1 | 9/2019 | Li et al. |
| 2019/0287376 A1 | 9/2019 | Netscher |
| 2019/0287676 A1 | 9/2019 | Kaplan |
| 2019/0318283 A1 | 10/2019 | Kelly |
| 2019/0319813 A1 | 10/2019 | Abu-Ghazaleh |
| 2019/0320900 A1 | 10/2019 | Majmudar |
| 2019/0325502 A1 | 10/2019 | Tovey |
| 2019/0334907 A1 | 10/2019 | Rodden |
| 2019/0362319 A1 | 11/2019 | Yen |
| 2019/0362858 A1 | 11/2019 | Valentino et al. |
| 2019/0388017 A1 | 12/2019 | Keating |
| 2019/0392489 A1 | 12/2019 | Tietzen |
| 2020/0005928 A1 | 1/2020 | Daniel |
| 2020/0019852 A1 | 1/2020 | Yoon |
| 2020/0020165 A1 | 1/2020 | Tran |
| 2020/0020454 A1 | 1/2020 | McGarvey |
| 2020/0043077 A1 | 2/2020 | Turner |
| 2020/0051573 A1 | 2/2020 | Jones et al. |
| 2020/0058381 A1 | 2/2020 | Patel |
| 2020/0074382 A1 | 3/2020 | Olsen |
| 2020/0097131 A1 | 3/2020 | Bowden et al. |
| 2020/0121544 A1 | 4/2020 | George |
| 2020/0126670 A1 | 4/2020 | Bender |
| 2020/0143655 A1 | 5/2020 | Gray |
| 2020/0151277 A1 | 5/2020 | Fisher |
| 2020/0160428 A1 | 5/2020 | Calvo |
| 2020/0272998 A1 | 8/2020 | Jameson et al. |
| 2020/0286310 A1 | 9/2020 | Carver et al. |
| 2020/0302549 A1 | 9/2020 | Jordan, II |
| 2020/0311682 A1 | 10/2020 | Olshansky |
| 2020/0312113 A1 | 10/2020 | Victor |
| 2020/0327791 A1 | 10/2020 | Moon |
| 2020/0335183 A1 | 10/2020 | Tommasi et al. |
| 2020/0341593 A1 | 10/2020 | Han et al. |
| 2020/0349632 A1 | 11/2020 | Xu |
| 2020/0365264 A1 | 11/2020 | Girardeau et al. |
| 2021/0019694 A1 | 1/2021 | Dhesi |
| 2021/0035432 A1 | 2/2021 | Moon |
| 2021/0042843 A1 | 2/2021 | Bryant |
| 2021/0043058 A1 | 2/2021 | Williams |
| 2021/0158671 A1 | 5/2021 | Jordan, II |
| 2021/0174916 A1 | 6/2021 | Ginsburg et al. |
| 2021/0312528 A1 | 10/2021 | Benkreira et al. |
| 2021/0335115 A1 | 10/2021 | Williams |
| 2021/0358618 A1 | 11/2021 | Crocker |
| 2022/0019518 A1 | 1/2022 | Marcin et al. |
| 2022/0031239 A1 | 2/2022 | Curtis |
| 2022/0092669 A1 | 3/2022 | Abrahamian et al. |
| 2022/0114210 A1 | 4/2022 | Kessler |
| 2022/0114640 A1 | 4/2022 | Pawar |
| 2022/0159344 A1 | 5/2022 | Gutierrez |
| 2022/0310079 A1 | 9/2022 | Kalns et al. |
| 2022/0353565 A1 | 11/2022 | Chow et al. |
| 2022/0355802 A1 | 11/2022 | Chaves |

FOREIGN PATENT DOCUMENTS

| JP | 2013179381 A | 9/2013 |
| JP | 2014056423 A | 3/2014 |
| JP | 2014142889 A | 8/2014 |
| JP | 2017116994 A | 6/2017 |
| WO | 2009061936 A1 | 5/2009 |
| WO | WO-2011133628 A1 * | 10/2011 | ............ G16H 20/10 |
| WO | 2014106294 A1 | 7/2014 |
| WO | 2019086849 A1 | 5/2019 |
| WO | 2019246239 A1 | 12/2019 |
| WO | 2020010217 A1 | 1/2020 |

OTHER PUBLICATIONS

Easton, Katherine et al.; A Virtual Agent to Support Individuals Living With Physical and Mental Comorbidities: Co-Design and Acceptability Testing; J Med Internet Res. May 30, 2019;21(5): e12996 (Year: 2019) (Year: 2019).*

Marcelino I, Lopes D, Reis M, Silva F, Laza R, Pereira A. Using the eServices platform for detecting behavior patterns deviation in the elderly assisted living: a case study. Biomed Res Int. 2015;2015:530828. doi: 10.1155/2015/530828. Epub Mar. 22, 2015. PM ID: 25874219; PMCID: PMC4385593. (Year: 2015).

Pradhan et al. ; "Accessibility Came by Accident'- Use of Voice-Controlled Intelligent Personal Assistants by People with Disabilities." Proceedings of the 2018 CHI Conference on human factors in computing systems; 2018.

How to Protect Personal Information Online; Jun. 29, 2020; Carnegie Mellon University Information Security Office Computing Services (Year: 2020).

Robben et al. (2012). How Is Grandma Doing Predicting Functional Health Status from Binary Ambient Sensor Data. AAAI Fall Symposium: Artificial Intelligence for Gerontechnology. 6 p.

Robben et al. (2014). Expert knowledge for modeling the relation between functional health and data from ambient assisted living sensor systems. Poster session presented at 10th Congress of the

(56)             References Cited

OTHER PUBLICATIONS

European Union of Geriatric Medicine Society (EUGMS) 2014, Rotterdam. https://www.thieme-connect.com/products/ejournals/abstract/10.3414/ME15-01-0072, 1 p.

Robben et al. (2016). Delta Features From Ambient Sensor Data are Good Predictors of Change in Functional Health. IEEE Journal of Biomedical and Health Informatics. 21. 1-1. 10.1109/JBHI.2016.2593980. 8 p.

S. A. Becker and F. Webbe, "Use of Handheld Technology by Older Adult Caregivers as Part of a Virtual Support Network," 2006 Pervasive Health Conference and Workshops, 2006, pp. 1-10, doi: 10.1109/PCTHEALTH.2006.361697.

S. Jiang, Y. Cao, S. Iyengar, P. Kuryloski, R. Jafari, Y. Xue, R. Bajcsy, S. Wicker. "CareNet: An Integrated Wireless Sensor Networking Environment for Remote Healthcare," Proceedings of the 3rd International Conference on Body Area Networks (BODYNETS 2008), Mar. 13-15, 2008.

Seelye et al., "Passive Assessment of Routine Driving with Unobtrusive Sensors: A New Approach for Identifying and Monitoring Functional Level in Normal Aging and Mild Cognitive Impairment", Journal of Alzheimers Disease, 59, 10.3233/JAD-170116., 2017, 19 p.

Sprint et al. (2016). Using Smart Homes to Detect and Analyze Health Events. Computer. 49. 29-37. 10.1109/MC.2016.338. 12 p.

Sprint et al. Analyzing Sensor-Based Time Series Data to Track Changes in Physical Activity during Inpatient Rehabilitation. Sensors (Basel). Sep. 27, 2017;17(10):2219. doi: 10.3390/s17102219. PMID: 28953257; PMCID: PMC5677114. 20 p.

Su et al., "Radar placement for fall detection: Signature and performance", Journal of Ambient Intelligentce and Smart Environments, 2018, 10.3233/AIS-170469, 14 p.

Tesla. (Dec. 6, 2018). Discover Software Version 9.0. Retrieved from Tesla Corporation Website: https://www.tesla.com/support/software-v9.

The Accuracy Of Self-Reported Data Of An Aging Population Using A Telehealth System In A Retirement Community Setting Based On The Users Age, Gender, Employment Status And Computer Experience, Gurley, Kelley Anne. University of Maryland, Baltimore.

Yildirim et al., Fall detection using smartphone-based application, International Journal of Applied Mathmatics Electronics and Computers 4, No. 4, 2016.

Yu et al. A posture recognition-based fall detection system for monitoring an elderly person in a smart home environment, IEEE transactions on Information Technology in Biomedicine 16, No. 6: 1274-1286.

Microsoft Community, "How to replace a video section but retain the audio in Windows Movie Maker?", Apr. 19, 2009, <https://answers.microsoft.com/en-us/windows/forum/all/how-to-replace-a-video-section-but-retain-the/a79384d0-64cf-40b1-8f25-a1091a4267fd> (Year: 2009).

"Elderly Alexa helps families care for their loved ones via voice", Perez, Sarah, techcrunch.com, May 14, 2017 (Year: 2017).

"Elderly Alexa helps families care for their remote loved ones via voice", reposted by Northeastern Global News, May 14, 2017, 3 p.

"Elderly-Alexa", TechCrunch video retrieved from https://techcrunch.com/unified-video/elderly-alexa/, May 14, 2017, 12 p.

"Eldery-Alexa" TechCrunch article retrieved from https://techcrunch.com/unified-video/elderly-alexa/, May 14, 2017, 7 p.

"Facilitating Elders Aging in Place: The 2017 Enterprise Management Hackathon", retrieved from https://mitsloan.mit.edu/sites/default/files/inline-files/2017_EMTrack_Hackathon_article.pdf, 4 p.

"How to use Alexa Care Hub to help monitor and contact older relatives or friends", Dave Johnson, Business Insider, Jan. 14, 2021, https://www.businessinsider.com/how-to-use-alexa-care-hub.

Aicha, A.N. et al., "Continuous measuring of the indoor walking speed of older adults living alone", J Ambient Intell Human Comput, 2018, 9:589-599, 11 p.

Akl et al. Unobtrusive Detection of Mild Cognitive Impairment in Older Adults Through Home Monitoring. IEEE J Biomed Health Inform. Mar. 2017;21(2):339-348. doi: 10.1109/JBHI.2015.2512273. Epub Dec. 24, 2015. PMID: 26841424; PMCID: PMC4919247. 22 p.

Amazons Care Hub will see success due to swelling interest in aging at home"and boosted smart speaker adoption", Zoe LaRock, Nov. 13, 2020, https://www.businessinsider.com/amazon-care-hub-will-succeed-amid-growing-smart-speaker-adoption-2020-11.

Apple. (2018, Dec. 17). SilverSneakers GO. Retrieved from Itunes App Store: https://itunes.apple.com/us/app/silversneakers-go/id1410437380mt=8.

Apple. (Dec. 6, 2018). App Store. Retrieved from Apple Web Site: https://www.apple.com/ios/app-store/.

Apple. (Dec. 6, 2018). DVD Netflix. Retrieved from iTunes App Store Preview: https://itunes.apple.com/us/app/dvd-netflix/id1169772776mt=8.

Austin et al., "A Smart-Home System to Unobtrusively and Continuously Assess Loneliness in Older Adults", IEEE Journal of Translational Engineering in Health and Medicine, 2016, doi: 10.1109/JTEHM.2016.2579638. PMID: 27574577; PMCID: PMC4993148, 11 p.

Austin et al., "Variability in medication taking is associated with cognitive performance in nondemented older adults", Alzheimers and Dementia: Diagnosis, Assessment and Disease Monitoring, 2017, doi: 10.1016/j.dadm.2017.02.003. PMID: 28349120; PMCID: PMC5358531, 4 p.

Austin, Daniel et al., "Unobtrusive monitoring of the longitudinal evolution of in-home gait velocity data with applications to elder care", Conf Proc IEEE Eng Med Biol Soc., 2011; 2011:6495-8. doi: 10.1109/IEMBS.2011.6091603. PMID: 22255826; PMCID: PMC3402166. 9 p.

Banerjee et al., "Exploratory analysis of older adults" sedentary behavior in the primary living area using kinect depth data, Journal of Ambient Intelligence and Smart Environments, 9, 163-179, 10.3233/AIS-170428, 2017, 18 p.

Bouwer, Julia. Evaluating eWALL: Assessing and enhancing older adults acceptance of a protoype smart home technology, Jan. 2015, retrieved from https://essay.utwente.nl/69042/1/Bouwer_BA_BMS.pdf , 59 p.

C. R. Costa, L. E. Anido-RifOn and M. J. Fernandez-Iglesias, "An Open Architecture to Support Social and Health Services in a Smart TV Environment," in IEEE Journal of Biomedical and Health Informatics, vol. 21, No. 2, pp. 549-560, Mar. 2017, doi: 10.1109/JBHI.2016.2525725 (Year: 2017).

Canary Care How It Helps page retrieved from https://web.archive.org/web/20190322142707/canarycare.co.uk/how-it-helps/, Mar. 22, 2019, 10 p.

Canary Care How it works page retrieved from https://web.archive.org/web/20190322142414/https://www.canarycare.co.uk/how-it-works/, Mar. 22, 2019, 9 p.

Chung et al., "Feasibility testing of a home-based sensor system to monitor mobility and daily activities in Korean American older adults", Int J Older People Nurs. Mar. 2017; 12(1). doi: 10.1111/opn.12127. PMID: 27431567. 31 p.

D. J. Cook et al., "MavHome: an agent-based smart home," Proceedings of the First IEEE International Conference on Pervasive Computing and Communications, 2003 (PerCom 2003), Fort Worth, TX, pp. 521-524, doi: 10.1109/PERCOM.2003.1192783, 15 p.

Dawadi et al., "Automated Cognitive Health Assessment From Smart Home-Based Behavior Data", IEEE J Biomed Health Inform. Jul. 2016;20(4):1188-94. doi: 10.1109/JBHI.2015.2445754, PMID: 26292348; PMCID: PMC4814350, 38 p.

E. Leinonen, A. Firouzian, C. Partanen and p. Pulli, "Visual validation services with time coordination for senior citizens social events—OldBirds digital twin platform," 2019 IEEE International Conference on Engineering, Technology and Innovation (ICE/ITMC), 2019, pp. 1-7, doi: 10.1109/ICE.2019.8792663.

Edison et al. (2017). Challenges and Opportunities in Automated Detection of Eating Activity. In: Rehg, J., Murphy, S., Kumar, S. (eds) Mobile Health. Springer, Cham. 24 p.

EWall for Active Long Living, Initial Scenarios and Use-Cases, Deliverable D2.2 version 1 retrieved from https://cordis.europa.eu/docs/projects/cnect/8/610658/080/deliverables/001-eWALLD22v10.pdf , Feb. 28, 2014, 74 p.

(56)          References Cited

OTHER PUBLICATIONS

Fritz et al., "Identifying Varying Health States in Smart Home Sensor Data : An Expert-Guided Approach", 2017, 6 p.

H. Wang, Q. Zhang, M. Ip and J. T. Fai Lau, "Social Media-based Conversational Agents for Health Management and Interventions," in Computer, vol. 51, No. 8, pp. 26-33, Aug. 2018, doi: 10.1109/MC.2018.3191249 (Year: 2018).

Hellmers et al., "Towards a minimized unsupervised technical assessment of physical performance in domestic environments", In Proceedings of the 11th EAI International Conference on Pervasive Computing Technologies for Healthcare (PervasiveHealth 2017), Association for Computing Machinery, New York, NY, USA, 207-216. 10 p.

J. Anish Dev, "Bitcoin mining acceleration and performance quantification," 2014 IEEE 27th Canadian Conference on Electrical and Computer Engineering (CCECE), 2014, pp. 1-6 (Year: 2014).

Jeff Johnson, "Designing User Interfaces for an Aging Population", Feb. 2017 | Talks at Google. Retrieved from Youtube: https://www.youtube.com/watchv=czjksAESHAo, Abstract only.

Kaye JA et al., "Intelligent Systems For Assessing Aging Changes: home-based, unobtrusive, and continuous assessment of aging",The Journals of Gerontology, Series B: Psychological Sciences and Social Sciences, 2011 i180-90, doi: 10.1093/geronb/gbq095, PMID: 21743050; PMCID: PMC3132763, 11 p.

Kyriazakos, S., Prasad, R., Mihovska, A. et al. eWALL: An Open-Source Cloud-Based eHealth Platform for Creating Home Caring Environments for Older Adults Living with Chronic Diseases or Frailty. Wireless Pers Commun 97, 1835-1875 (2017). 65 p.

Marscarenhas, Natasha, "BostonInno Approved: The Weeks Top Tech Startup Events in Boston", Mar. 17, 2017, 5 p.

Mengxuan et al., "Assistive Adjustable Smart Shower System," 2017 IEEE/ACM International Conference on Connected Health: Applications, Systems and Engineering Technologies (CHASE), Philadelphia, PA, USA, 2017, pp. 253-254, doi: 10.1109/CHASE.2017.89, 2 p.

Mengxuan, Ma et al., "VicoVR-Based Wireless Daily Activity Recognition and Assessment System for Stroke Rehabilitation," 2018 IEEE International Conference on Bioinformatics and Biomedicine (BIBM), Madrid, Spain, 2018, pp. 1117-1121, doi: 10.1109/BIBM.2018.8621151, 5 p.

Mozer, Michael C.. "The Neural Network House: An Environment that Adapts to its Inhabitants." Proceedings of the American Association for Artificial Intelligence Spring Symposium on Intelligent Environments, (1998), 5 p.

Nashville Post, "Seniors have increasingly become more tech savvy", Aug. 28, 2017, available at https://www.nashvillepost.com/business/people/seniors-have-increasingly-become-more-tech-savvy/article_2e047f87-8872-5d1e-b2cb-5be6392f9efd.html, 4 p.

Newland et al., "Continuous In-Home Symptom and Mobility Measures for Individuals With Multiple Sclerosis: A Case Presentation", Journal of Neuroscience Nurses, Aug. 2017; 49(4):241-246. doi: 10.1097/JNN.0000000000000299. PMID: 28661948. 6 p.

Nunez-Marcos et al., Vision-based fall detection with convolutional neural networks, Wireless and Communications and Mobile Computing, vol. 2017, Article ID 9474806, 16 pgs.

Orcatech Research Studies available at https://www.ohsu.edu/oregon-center-for-aging-and-technology/orcatech-research-studies, retrieved on Jul. 2, 2023, 4 p.

P. Kuryloski, S. Pai, S. Wicker, Y. Xue, "MedSN System for In-Home Patient Monitoring: Architecture, Privacy and Security" Proceedings of the Joint Conference on High Confidence Medical Devices, Software, and Systems (HCMDSS07) and Medical Device Plug-a.

Parde, Natalie; Reading with Robots: A Platform to Promote Cognitive Exercise Through Identification and Discussion of Creative Metaphor in Books; : University of North Texas. ProQuest Dissertations Publishing, 2018. 11005488. (Year: 2018).

Perez, Sarah, Elderly Alexa helps families care for their remote loved ones via voice, TechCrunch, May 14, 2017, 8 p.

Petersen et al., "Time Out-of-Home and Cognitive, Physical, and Emotional Wellbeing of Older Adults: A Longitudinal Mixed Effects Model", PLoS One. Oct. 5, 2015;10(10):e0139643. doi: 10.1371/journal.pone.0139643. PMID: 26437228; PMCID: PMC4593630. 16 p.

Pirzada et al, Sensors in Smart Homes for Independent Living of the Elderly, 2018, 2018 5th International Multi-Topic ICT Conference (IMTIC) (Year: 2018).

PubNub, "4 Game Changers from the TechCrunch Disrupt Hackathon", May 5, 2017, 15 p.

Rantz et al., "Randomized Trial of Intelligent Sensor System for Early Illness Alerts in Senior Housing", J Am Med Dir Assoc. Oct. 1, 2017;18(10):860-870. doi: 10.1016/j.jamda.2017.05.012. Epub Jul. 12, 2017. PMID: 28711423; PMCID: PMC5679074. 28 p.

Riboni et al., "Fine-grained recognition of abnormal behaviors for early detection of mild cognitive impairment," 2015 IEEE International Conference on Pervasive Computing and Communications (PerCom), St. Louis, MO, USA, 2015, pp. 149-154, doi: 10.1109/PERCOM.2015.7146521. 10 p.

Riboni et al., "Extended Report: Fine-grained recognition of abnormal behaviors for early detection of mild cognitive impairment," 2015 IEEE International Conference on Pervasive Computing and Communications (PerCom), St. Louis, MO, USA, 2015, pp. 149-154, doi: 10.1109/PERCOM.2015.7146521. 10 p.

Dawadi et al., "Automated Clinical Health Assessment From Smart Home-Based Behavior Data", IEEE J Biomed Health Inform. Jul. 2016;20(4):1188-94. doi: 10.1109/JBHI.2015.2445754, PMID: 26292348; PMCID: PMC4814350, 38 p.

Alpaydin, Ethem "Introduction to Machine Learning" (3d ed. 2014) 640 p.

"Amazon Introduces the Alexa Skills Kit—A Free SDK for Developers," available at https://press.aboutamazon.com/2015/6/amazon-introduces-the-alexa-skills-kit-a-free-sdk-for-developers; Jun. 25, 2015; 7 pp.

"Announcing New Alexa Skills Kit (ASK) Features: Account Linking and Service Simulator," available at https://developer.amazon.com/en-us/blogs/alexa/post/Tx7MF6PV44SOXU/announcing-new-alexa-skills-kit-ask-features-account-linking-and-service-simulato.html; Sep. 4, 2015; 3 pp.

"2015 Year in Review: More than 130 Skills On Alexa [Infographic]," available at https://developer.amazon. com/en-us/blogs/alexa/post/Tx2V9VQZDG9IXX/2015-year-in-review-more-than-130-skills-on-alexa-infographi.html; Jan. 7, 2016; 2 pp.

"Amazon Announces HIPAA-Compliant Alexa Skills, Opening Possibilities for Senior Living," available at https://seniorhousingnews.com/2019/04/04/amazon-announces-hipaa-compliant-alexa-skills-opening-possibilities-for-senior-living/; Apr. 4, 2019; 4 pp.

"Ask My Buddy," available at https://www.amazon.com/Beach-Dev-Ask-My-Buddy/dp/B017YAF22Y; 2 pp.

"OnGuardian Wins Top Prize," available at https://www.onguardian.io/test-post/; 1 p.

"OnGuardian Selected as Finalist at Aging2.0 Global Startup Search," available at https://www.onguardian.io/new-post/; 2 pp.

"Exciting Update: Unveiling Our Latest Video Overview of OnGuardian for Communities!"; available at https://www.onguardian.io/category/news/; 1 p.

OnGuardian by OnGuardian Apps LLC; https://www.amazon.com/OnGuardian-Apps-LLC/dp/B06XGTJ549; 3 pp.

User Guide-Registration and Setup; https://www.onguardian.io/new-post-2/; 2 pp.

"Exciting Update: Unveiling Our Latest Video Overview of OnGuardian for Communities!"; available at https://www.onguardian.io/exciting-update-unveiling-our-latest-video-overview-of-onguardian-for-communities/; 6 pp.

Ho, Annabell Suh; Understanding the Impact of Conversational AI on Supportive Interactions: Towards the Care (Conversational AI and Response Effects) Model; Stanford University, ProQuest Dissertations & Theses, 2018.28330492. ; (Year: 2018).

Adobe. Adobe Premiere Elements Help. Sep. 15, 2015. 273 pages. https://helpx.adobe.com/archive/en/premiere-elements/14/ premiere-elements_reference.pdf (Year: 2015).

Reddit question How to replace 5 seconds of video with a still image? (Premiere Elements 14) asked by jasonrumohrlmt. 2 pages

(56) References Cited

OTHER PUBLICATIONS https://www.reddit.com/r/VideoEditing/comments/jeu391/how_to_
replace_5_seconds_of_video_with_a_still/ (Year: 2021).
Pradhan et al. ("Accessibility Came by Accident' Use of Voice-
Controlled Intelligent Personal Assistants by People with Disabili-
ties. " Proceedings of the 2018 CHI Conference on human factors
in computing systems. 2018) (Year: 2018).

* cited by examiner

402   Register a user

404   Register a caregiver associated with the user

406   Receive input defining at least one event associated with the user

408   Assign the at least one event to the caregiver

410   Create a care schedule of the user

412   Display, via an application, the care schedule

400

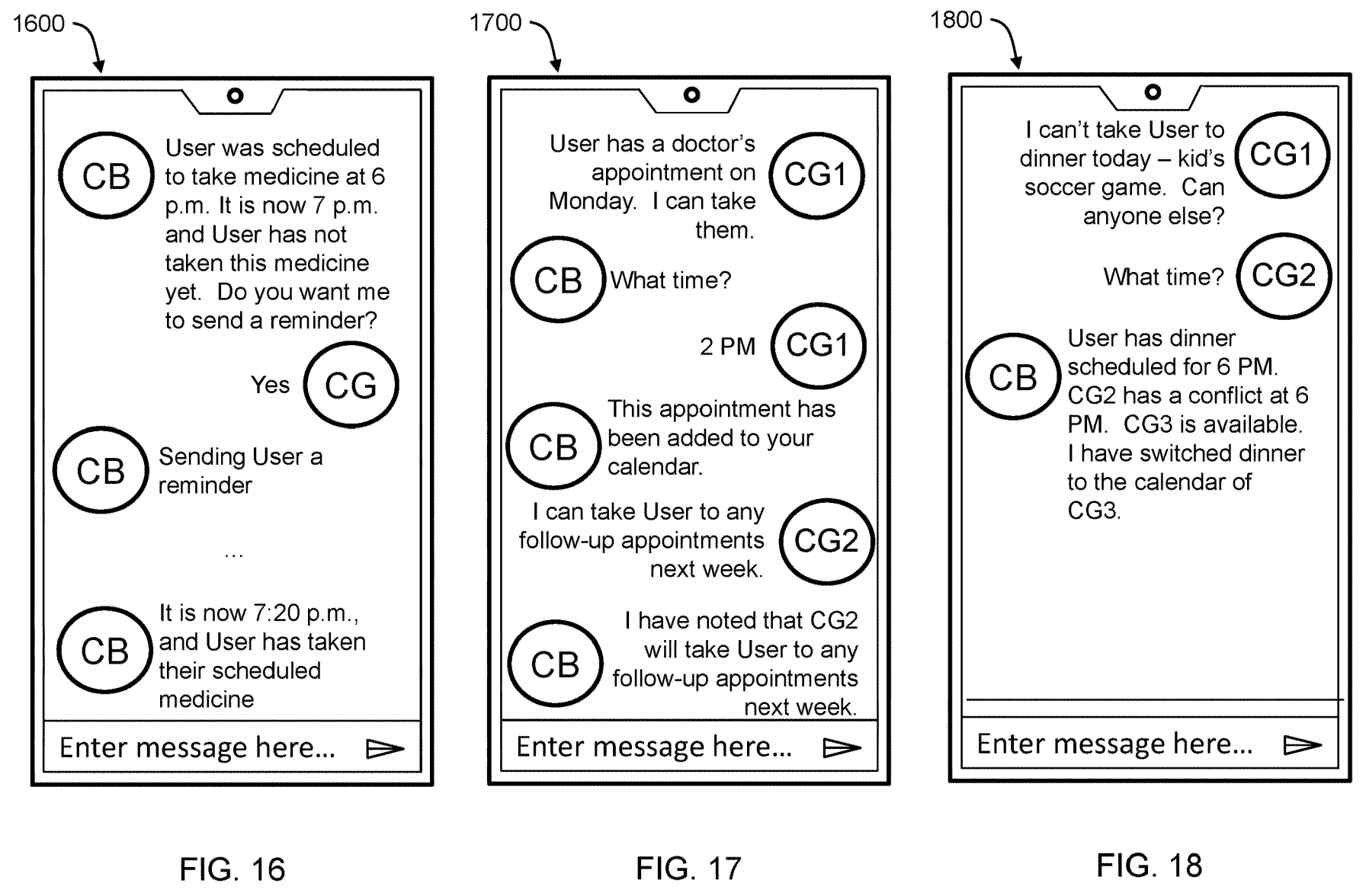

1800

CG1 I can't take User to dinner today – kid's soccer game. Can anyone else?

CG2 What time?

CB User has dinner scheduled for 6 PM. CG2 has a conflict at 6 PM. CG3 is available. I have switched dinner to the calendar of CG3.

Enter message here...

CG1 User has a doctor's appointment on Monday. I can take them.

CB What time?

CG1 2 PM

CB This appointment has been added to your calendar.

CB I can take User to any follow-up appointments next week.

CG2 I have noted that CG2 will take User to any follow-up appointments next week.

Enter message here...

CB User was scheduled to take medicine at 6 p.m. It is now 7 p.m. and User has not taken this medicine yet. Do you want me to send a reminder?

CG Yes

CB Sending User a reminder

...

CB It is now 7:20 p.m., and User has taken their scheduled medicine

Enter message here...

FIG. 16

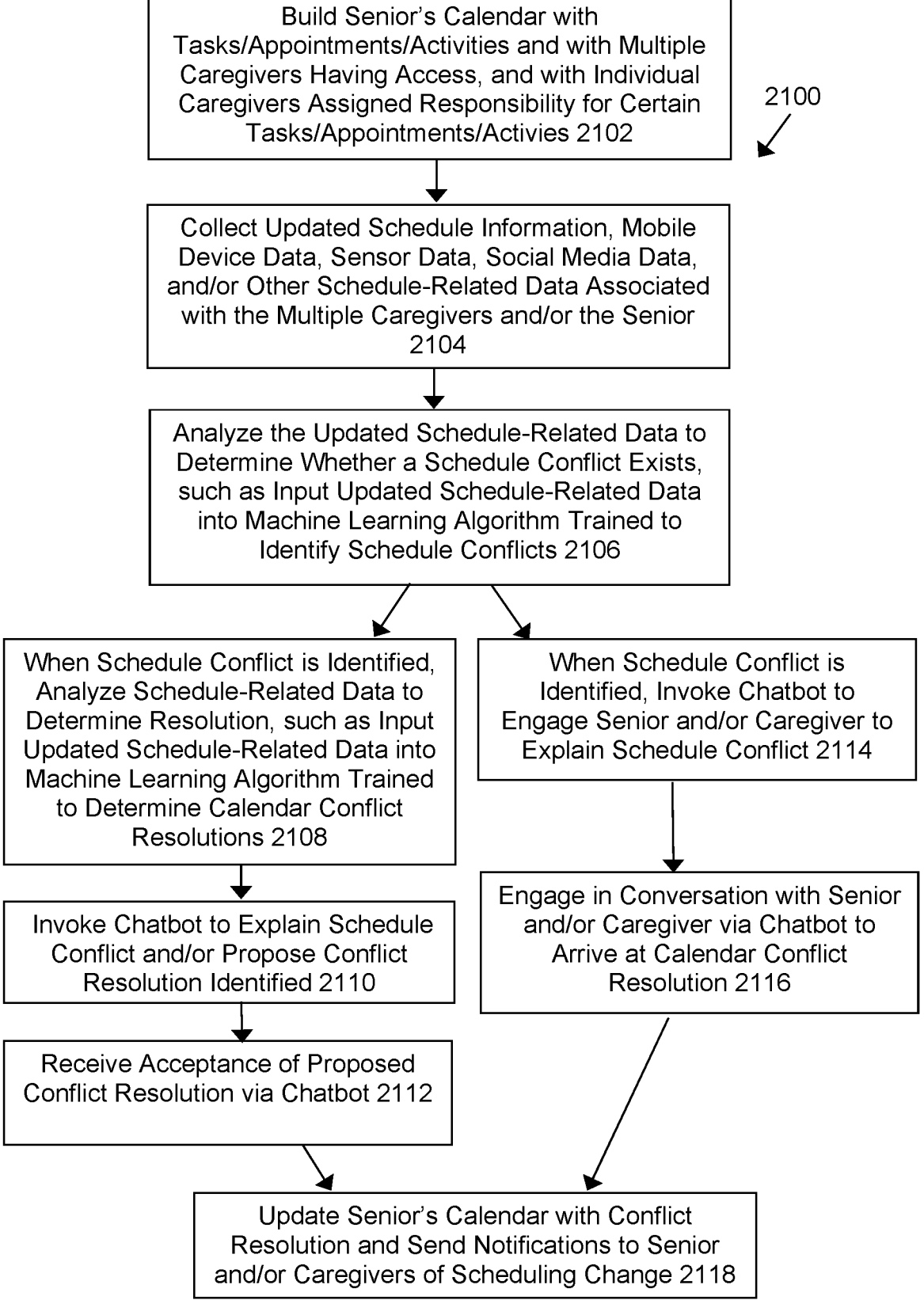

2100

Build Senior's Calendar with Tasks/Appointments/Activities and with Multiple Caregivers Having Access, and with Individual Caregivers Assigned Responsibility for Certain Tasks/Appointments/Activies 2102

Collect Updated Schedule Information, Mobile Device Data, Sensor Data, Social Media Data, and/or Other Schedule-Related Data Associated with the Multiple Caregivers and/or the Senior 2104

Analyze the Updated Schedule-Related Data to Determine Whether a Schedule Conflict Exists, such as Input Updated Schedule-Related Data into Machine Learning Algorithm Trained to Identify Schedule Conflicts 2106

When Schedule Conflict is Identified, Analyze Schedule-Related Data to Determine Resolution, such as Input Updated Schedule-Related Data into Machine Learning Algorithm Trained to Determine Calendar Conflict Resolutions 2108

When Schedule Conflict is Identified, Invoke Chatbot to Engage Senior and/or Caregiver to Explain Schedule Conflict 2114

Invoke Chatbot to Explain Schedule Conflict and/or Propose Conflict Resolution Identified 2110

Engage in Conversation with Senior and/or Caregiver via Chatbot to Arrive at Calendar Conflict Resolution 2116

Receive Acceptance of Proposed Conflict Resolution via Chatbot 2112

Update Senior's Calendar with Conflict Resolution and Send Notifications to Senior and/or Caregivers of Scheduling Change 2118

FIGURE 21

SENIOR LIVING CARE COORDINATION PLATFORMS

CROSS-REFERENCE TO RELATED APPLICATIONS

This application claims priority to and is a continuation of U.S. patent application Ser. No. 16/913,937, filed Jun. 26, 2020, entitled "SENIOR LIVING CARE COORDINATION PLATFORMS," which claims priority to U.S. Provisional Patent Application Ser. No. 62/870,515, filed Jul. 3, 2019, entitled "SENIOR LIVING CARE COORDINATION PLATFORMS," U.S. Provisional Patent Application Ser. No. 62/872,014, filed Jul. 9, 2019, entitled "SENIOR LIVING CARE COORDINATION PLATFORMS," and to U.S. Provisional Patent Application Ser. No. 62/874,258, filed Jul. 15, 2019, entitled "SENIOR LIVING CARE COORDINATION PLATFORMS," the entire contents and disclosures of which are hereby incorporated herein by reference in their entirety.

FIELD OF THE INVENTION

The present disclosure relates to senior living computer platforms and, more particularly, to systems and methods for using a senior living computer platform to coordinate a care schedule for a senior user, wherein the care schedule includes schedules of caregivers and other service providers for the senior user.

BACKGROUND

At least some conventional computer networks (e.g., matching platforms) have enabled caregivers (e.g., family members, friends, and care service providers) associated with senior users to coordinate care for the senior user. However, conventional systems usually merely keep a schedule of the coordinated care, and may not provide additional functionality. Further, in the conventional systems, caregivers may have to coordinate the care between the other caregivers before the caregivers can prepare a schedule. Known systems may have other drawbacks as well.

BRIEF SUMMARY

The present embodiments may relate to systems and methods for electronically coordinating and maintaining a care schedule of a senior user for caregivers associated with helping the senior user. The system may include a care coordination support computing device, one or more client devices, one or more chatbot servers, one or more sensor servers, and/or one or more databases.

In one aspect, a care coordination support platform ("CCSP") computer system for coordinating care may be provided. The CCSP computer system may include at least one processor in communication with at least one chatbot and at least one memory device, and the at least one processor may be programmed to: (i) register a user through an application, wherein the user inputs personal and scheduling data into the application, (ii) register a caregiver associated with the user through the application, wherein the caregiver inputs personal and scheduling data into the application, and wherein the caregiver is one caregiver out of a plurality of caregivers associated with the user, (iii) receive input from at least one of the user and the caregiver defining at least one event associated with the user, wherein the event includes at least one of a task, an activity, and an appointment, (iv) assign the at least one event to at least one caregiver of the plurality of caregivers based upon the personal and scheduling data of the plurality of caregivers, (v) create a care schedule of the user, wherein the care schedule of the user includes the at least one assigned event, (vi) display, via the application, the care schedule to the at least one caregiver on at least one device associated with the at least one caregiver, (vii) receive, via the chatbot, a question regarding the at least one event from at least one of the user and the caregiver, wherein the question is at least one of a natural-language typed question and a natural-language voice question, (viii) convert, via the chatbot, the question into a query, (ix) run, via the chatbot, the query against an event database stored in the at least one memory device, and (x) transmit, via the chatbot, a response to the question to the processor, wherein the response includes an answer to the question, in response to the query returning the at least one event. The CCSP computer system may include additional, less, or alternate functionality, including that discussed elsewhere herein.

In another aspect, a care coordination support platform ("CCSP") computer system for coordinating care may be provided. The CCSP computer system may include at least one processor and/or associated transceiver in communication with at least one memory device, and the at least one processor and/or associated transceiver may be programmed to: (i) register a senior through an application, wherein the senior inputs personal and scheduling data into the application, (ii) register multiple caregivers associated with the senior through the application, wherein each caregiver inputs personal and scheduling data into the application, (iii) receive input from at least one of the senior and the caregiver defining at least one event associated with the senior, wherein the event includes at least one of a task, an activity, and an appointment, (iv) assign the at least one event to at least one caregiver of the multiple caregivers based upon the personal and scheduling data of the multiple caregivers, (v) create a care schedule of the senior, wherein the care schedule of the senior includes the at least one assigned event, (vi) receive updated scheduling-related data associated with the senior and/or the multiple caregivers, and (vii) compare the care schedule of the senior with the updated scheduling-related data to determine a calendar conflict associated with the senior and/or at least one caregiver. The CCSP computer system may include additional, less, or alternate functionality, including that discussed elsewhere herein.

In yet another aspect, a computer-implemented method for coordinating care may be provided. The computer-implemented method may be performed by a care coordination support platform ("CCSP") computer system including at least one processor in communication with at least one chatbot and at least one memory device. The computer-implemented method may comprise: (i) registering a user through an application, wherein the user inputs personal and scheduling data into the application, (ii) registering a caregiver associated with the user through the application, wherein the caregiver inputs personal and scheduling data into the application, and wherein the caregiver is one caregiver out of a plurality of caregivers associated with the user, (iii) receiving input from at least one of the user and the caregiver defining at least one event associated with the user, wherein the event includes at least one of a task, an activity, and an appointment, (iv) assigning the at least one event to at least one caregiver of the plurality of caregivers based upon the personal and scheduling data of the plurality of caregivers, (v) creating a care schedule of the user, wherein the care schedule of the user includes the at least one assigned event, (vi) displaying, via the application, the care schedule to the at least one caregiver on at least one device associated with the at least one caregiver, (vii) receiving, via the chatbot, a question regarding the at least one event from at least one of the user and the caregiver, wherein the question is at least one of a natural-language typed question and a natural-language voice question, (viii) converting, via the chatbot, the question into a query, (ix) running, via the chatbot, the query against an event database stored in the at least one memory device, and (x) transmitting, via the chatbot, a response to the question to the processor, wherein the response includes an answer to the question, in response to the query returning the at least one event. The method may include additional, less, or alternate actions, including those discussed elsewhere herein.

BRIEF DESCRIPTION OF THE DRAWINGS

The Figures described below depict various aspects of the systems and methods disclosed therein. It should be understood that each Figure depicts an embodiment of a particular aspect of the disclosed systems and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and are instrumentalities shown, wherein:

FIGS. 6-20 are screenshots of one example of a care coordination support application illustrated in FIG. 1;

FIG. 21 illustrates an exemplary computer-implemented method for coordinating care and resolving schedule conflicts via a care coordination support platform ("CC SP") computer system.

Figure 1:
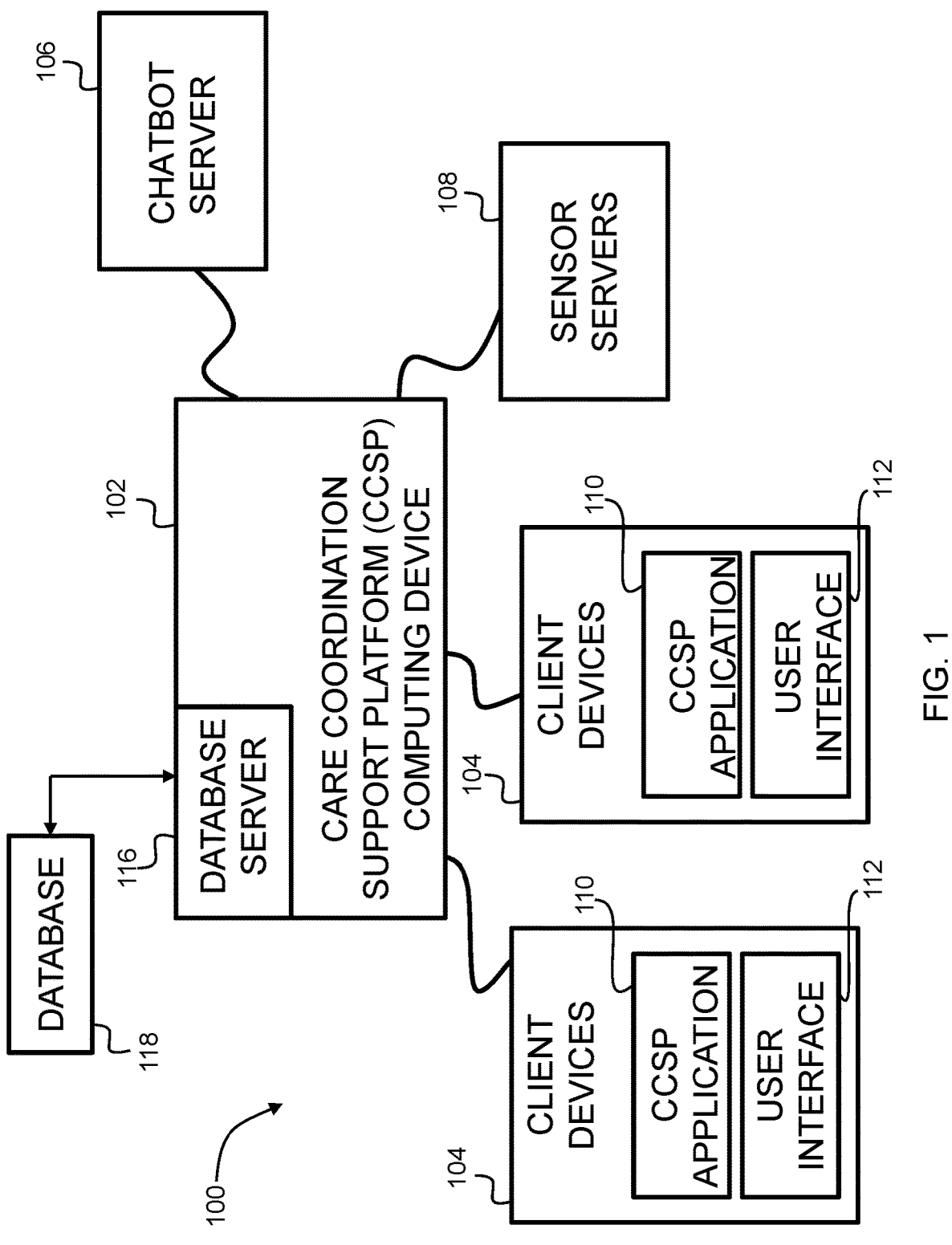
FIG. 1 illustrates an exemplary care coordination support computer system for electronically coordinating and maintaining a care schedule of users for caregivers in accordance with the present disclosure.

The Figures depict preferred embodiments for purposes of illustration only. One skilled in the art will readily recognize from the following discussion that alternative embodiments of the systems and methods illustrated herein may be employed without departing from the principles of the invention described herein.

DETAILED DESCRIPTION

The present embodiments may relate to, inter alia, systems and methods for electronically coordinating a care schedule of a senior user (also referred to herein as a "user") among one or more caregivers associated with the user. In one exemplary embodiment, the process may be performed by a care coordination support platform ("CCSP") computer system (also referred to herein as a "CCSP platform" and a "CCSP server").

As described below, the systems and methods described herein may leverage different types of data (e.g., user and caregiver data, user events including tasks, activities, and appointments, caregiver schedules, sensor data, and mobile device data) to determine and coordinate a care schedule of the user among one or more caregivers of the user. The systems and methods described herein may include a chatbot configured to assist in the determining and coordination of the care schedule of the user, and the chatbot may be configured to seamlessly aid caregivers in carrying out the care schedule of the user. In some embodiments, the chatbot may verbally explain scheduled events and/or schedule conflicts that may arise, and the chatbot may be configured to receive verbal responses to the chatbot from users and caregivers. In some embodiments, the user may be a senior who needs extra help going about their daily routines (e.g., rides to appointments, refills on their prescriptions, home and vehicle maintenance, emergency monitoring, and completion of tasks, like taking their medicine).

The caregivers associated with the user may include people who normally take care of the user (e.g., family members, friends, paid caregivers, etc.) and service providers of the user (e.g., health care professionals, such as doctors, nurses, physical therapists, occupational therapists, etc.). The caregivers often have busy schedules, and it may be difficult for the caregivers to coordinate caring for the user. Accordingly, friction between caregivers may arise from constantly trying to coordinate care and scheduling to take care of the user.

The systems and methods described herein ensure that each caregiver is able to care for the user and/or carry out tasks for the user and may reduce friction between caregivers by providing a platform that automatically assigns care duties to caregivers based upon information (e.g., scheduling and calendar information) input by the caregivers and ensures that the caregivers complete their assigned duties. Further, the systems and methods described herein may learn about the user and associated caregivers and adjust interactions with the user and associated caregivers and the coordinating of the care schedule of the user based upon the learning.

Exemplary User and Caregiver Data Collection

In the exemplary embodiment, a care coordination support platform (e.g., provided by a care coordination support platform server) may leverage different kinds of data (e.g., user and caregiver data, user events, caregiver schedules, sensor data, and mobile device data) to coordinate a care schedule of a user between one or more caregivers associated with the user. In the exemplary embodiment, a primary caregiver (e.g., an admin caregiver) may register for the care coordination support platform ("CCSP") service provided by a care coordination support platform ("CCSP") server through an application (e.g., a CCSP application) on a mobile device associated with the admin caregiver, or any other suitable device that may access the CCSP application and/or a website associated with the CCSP application.

In registering for the CCSP service, the admin caregiver may provide the CCSP server with information associated with the user. The information associated with the user may include user data (e.g., name, birthdate, height, weight, etc.), user tasks (e.g., taking medicine, bathing, eating, paying bills, getting groceries, car maintenance, home maintenance, etc.), user activities (e.g., social activities, like bingo and golfing, physical activities, like working out and keeping active, etc.), user appointments (e.g., recurring appointments like yearly physicals and bimonthly haircuts, etc.), user alert preferences (e.g., when and through which method users prefer to be alerted) and any other information associated with the user that may be useful to the CCSP server.

In other embodiments, the user may register for the service and provide the CCSP server with information themselves. Further, in registering for the CCSP service, the admin caregiver may invite other caregivers to be a part of a care team for the user. For example, the admin caregiver may provide the CCSP server with a list of emails and/or phone numbers of other caregivers who are associated with the user. The CCSP server may send an invitation link and/or code to the other caregivers instructing the other caregivers on how to sign up for the care team for the user associated with the admin caregiver.

Each caregiver, including the admin caregiver, may register themselves for the CCSP service. In registering for the CCSP service, the caregivers may provide the CCSP server with caregiver information (e.g., name, contact information, relationship to the user), caregiver schedule information (e.g., known work and/or activity schedules of the caregivers), caregiver alert preferences (e.g., when and through which method caregivers prefer to be alerted) and any other caregiver information that may be useful to the CCSP server. In some embodiments, the caregivers may link their digital calendars (e.g., provided on a mobile device associated with the caregiver) to the CCSP server such that the caregivers do not have to manually input scheduling data available to the CCSP server into the digital calendar. The user and the caregivers may update and/or edit the user and caregiver data at any time (e.g., through the CCSP application).

In the exemplary embodiment, if the caregiver is a person who normally takes care of the user and needs to view and/or be notified of the schedule of the user, the caregiver may fully register for the CCSP service. If the caregiver is a person who only provides certain services to the user (e.g., a doctor, nurse, physical therapist, occupational therapist, etc.), the caregiver may have very limited access to the CCSP service, and the CCSP server may have very limited access to the caregiver data (e.g., the CCSP server may simply receive calendar updates from the caregiver if an event related to the user is scheduled).

In the exemplary embodiment, the CCSP server may also be configured to receive sensor data from sensors associated with the user and/or the caregivers. For example, sensors may include smart home device sensors (e.g., AMAZON ALEXA, GOOGLE HOME, and/or RING doorbells), wearable device sensors (e.g., APPLE WATCH and FITBIT), smart device sensors (e.g., smart pillboxes), sensors associated with a mobile device of the user and caregivers (e.g., GPS sensors), and any other sensors. In the exemplary embodiment, the CCSP server may be configured to store the received data (e.g., user data, caregiver data, sensor data, etc.) in a memory.

Exemplary Determination of Critical Care Tasks

In the exemplary embodiment, the CCSP server may determine whether events (including and also referred to herein as tasks, activities, and/or appointments) of the user are critical or non-critical. The CCSP server may determine that events are critical if the events are vital to the user and/or maintaining a livelihood of the user (e.g., taking medicine, helping the user get out of bed, taking the user to important appointments, helping the user bathe, etc.), and the CCSP server may determine that events are non-critical if the events are non-vital to the user and/or maintaining the livelihood of the user (e.g., mowing the user's grass, taking the user to Bingo, getting the user's oil changed, etc.).

The CCSP server may automatically determine that events of the user are critical or non-critical (e.g., through a description of the event), or the user and/or caregiver may manually input that the events of the user are critical or non-critical. Further, the determination of critical events vs. non-critical events may have an impact on user and caregiver alert and/or notification (e.g., SMS texts, emails, phone calls, and/or push button notifications from CCSP application) preferences. For example, the user and caregivers may only prefer to receive alerts and/or notifications for critical events, rather than all events.

Exemplary Care Coordination

In the exemplary embodiment, the CCSP server may be configured to process all of the user and caregiver data (e.g., events of the user, and schedules and preferences of the caregivers) the CCSP server receives from the user and caregivers (e.g., through the CCSP application) and coordinate a care schedule of the user between the caregivers. The CCSP server may automatically assign each task, activity, and/or appointment of the user to the caregivers based upon the received caregiver data, and the received caregiver data may include caregiver preferences and schedules. For example, one caregiver associated with the user may be a hired caregiver who is the primary caregiver of the user, and the other caregivers associated with the user may be family and/or friends of the user who may take care of events of the user if there is a need to do so (e.g., if the primary caregiver is unavailable).

The CCSP server may process the caregiver data associated with the caregivers and compare the caregiver data to the task, activity, and appointment schedule of the user. Based upon the compared data, the CCSP server may assign each task, activity, and appointment of the user to each of the caregivers. For example, the CCSP server may assign the events to the primary caregiver first (based upon a schedule of the primary caregiver) and then assign the rest of the events not assigned to the primary caregiver to other caregivers based upon the schedules of the other caregivers.

Further, the CCSP server may assign some events to the user to carry out when the user does not need assistance with the events (e.g., taking medication and/or doing daily exercises). For example, the caregivers may prefer to assign the events of the user manually, and the CCSP server may assist the caregivers in manually assigning the events (e.g., through a chatbot, described below). Once the events have been assigned to the user and/or the caregivers, the CCSP server may create a care schedule of the user. The care schedule may include all of the user's events, and the user and/or caregiver assigned to the events. The care schedule may be stored in, for example, a care database, in a memory device associated with the CCSP server.

The CCSP server may determine if events of the care schedule of the user are taken care of by the assigned caregiver through, for example, sensor data received by the CCSP server. For instance, if a user is scheduled to take medicine at a certain time two times a day, the CCSP server may receive data from a sensor (e.g., a smart pillbox) associated with the user to determine if the pill box was opened at the certain scheduled times. Further, for example, if a caregiver is scheduled to take the user to a doctor's appointment at a certain time, the CCSP server may receive location data of the user and the caregiver (e.g., from mobile devices of the user and/or caregiver) to determine if the caregiver took the user to the doctor's appointment. Additionally, if the user is scheduled to receive a grocery delivery at a certain time, the CCSP server may receive sensor data (e.g., from a smart home device like a smart doorbell) to determine if the groceries were delivered for the user (e.g., through determining if the doorbell was rung and/or a delivery person showed up around the scheduled time).

If the CCSP server determines that a task, activity, and/or appointment has not been carried out, the CCSP server may alert (e.g., through the CCSP application) the user and/or caregivers based upon the user and caregiver data (e.g., alert preferences). Further, the CCSP server may notify the caregivers, based on the alert preferences of the caregivers, when a scheduled event has been carried out by the caregiver and/or others (e.g., service providers). In other embodiments, the user and caregivers may manually enter that the events of the user have been taken care of by the caregiver.

Exemplary Care Coordination Support Application

In the exemplary embodiment, a CCSP application is associated with the CCSP server. The CCSP application may be configured to receive user and caregiver data, display the care schedule of the user to the caregivers, and/or alert and/or notify the user and caregivers of assigned events. The CCSP application may be run on a device associated with the user and/or caregiver (e.g., a mobile device and/or laptop of the user or caregiver). The CCSP application may be configured to display the care schedule of the user based upon the preference of the user and caregivers. For example, the CCSP application may display a list of daily, weekly, and/or monthly tasks assigned to the user and/or caregivers, a calendar that marks when the user and/or caregiver has assigned events, and any other display method that allows the user and caregivers to easily see and interact with the care schedule of the user.

In the exemplary embodiment, the CCSP server may include a chatbot that is embedded in the CCSP application and has access to the information stored by the CCSP server (e.g., scheduled/assigned events, user data, caregiver data, etc.). The chatbot may be any suitable chatbot and/or robo-assist device that functions as described herein. The chatbot may assist the user and caregivers in adding, editing, and/or deleting user and caregiver data, coordinating care of the user between the caregivers, receiving information about the assigned care schedule, and/or receiving information about how the user and caregivers are carrying out the care schedule.

For example, instead of a user and/or caregiver having to manually input each event of the user, each notification request of the user and caregivers, and/or each schedule item of the caregivers, the user and caregivers may give instructions to the chatbot (e.g., through typing and/or speaking commands and/or questions using plain or colloquial language, rather than structured commands, into the chatbot through the CCSP application). Also, for example, if the user just added a daily medication to their routine, the user may instruct the chatbot to add the medication to the daily list of tasks for the user to carry out. Further, a caregiver may instruct the chatbot that the user's lawn needs to be mowed every week in the summer.

The chatbot may also be configured to passively assist in coordinating care for the user between the caregivers. For example, if the caregivers mostly have the care schedule of the user figured out and scheduled, the chatbot may be configured to monitor what the users and caregivers input into the chatbot and provide assistance if necessary.

For instance, if one caregiver inputs into the chatbot that the caregiver is taking the user to an appointment on Monday at 2 p.m., the chatbot may respond to the caregiver that the appointment is on their calendar. If another caregiver says that the caregiver is taking the user to breakfast on Tuesday at 10 a.m., the chatbot may respond to the caregiver that the event is not in their calendar and ask the caregiver if the caregiver would like the event added to their calendar. If the caregiver responds that the caregiver would like the event added to their calendar, the chatbot may cause the event to be added to the calendar of the caregiver.

The user and caregivers may also ask the chatbot questions, and the chatbot may, for example, convert the natural-language question of the user and caregivers into a query, run the query against a database (e.g., an event database stored in a memory device), and transmit a response to the question to the processor including an answer to the question, in response to the query returning the at least one event. For example, the user may ask the chatbot who is taking them to a haircut appointment or oil change appointment, and the caregiver may ask the chatbot to identify the last time the user had a bath.

The chatbot may also notify and/or send alerts to the user and caregivers based upon the user and caregiver alert preferences. For example, the chatbot may notify a caregiver that a user has not yet taken their medicine, and the chatbot may ask the caregiver if the caregiver would like the chatbot to send a reminder to the user to take their medicine. If the caregiver says yes, the chatbot may automatically cause the reminder to be sent to the user.

In the exemplary embodiment, the chatbot may further be configured to learn from the user and caregiver requests, responses, and/or questions. For example, if the chatbot often notifies a caregiver that the user forgets to take a nightly dose of medication, and the caregiver typically tells the chatbot to remind the user to take their medication in response to the notification from the chatbot, the chatbot may automatically cause the CCSP computing device to start reminding the user to take their nightly medicine dosage without input from the caregiver.

Further, the chatbot may be configured to verbally explain scheduled events, scheduling conflicts, and/or missed scheduled events that may arise to the user and/or caregivers. For example, if the chatbot determines that a scheduling conflict has arisen (e.g., the caregiver and/or the user are double-booked), the chatbot may verbally engage with the user and/or caregiver to explain the scheduling conflict. In verbally engaging with the user and/or caregiver, the chatbot may be configured to converse with the user and/or caregiver to resolve the scheduling conflict. Further, if the chatbot determines that a scheduled event was missed, the chatbot may verbally alert the user and/or caregiver of the missed event. In verbally alerting the user and/or caregiver, the chatbot may also be configured to converse with the user and/or caregiver to resolve and/or reschedule the missed event.

The CCSP server may further be configured to generate caregiver analytics, and the CCSP application may be configured to display the generated analytics to the user and caregivers. The CCSP server may generate activity hour, effort hour, and task distribution analytics for each caregiver and compare the analytics to the other caregivers. For example, the CCSP server may generate a chart of the time each caregiver spends caring for the user and/or the time each caregiver spends putting in effort to the care of the user for a predetermined period of time. The CCSP server may further generate a chart of a percentage of tasks for the user that each caregiver handles over the predetermined period of time.

Exemplary Care Coordination Support System

FIG. 1 depicts a view of an exemplary care coordination support platform ("CCSP") system 100 that may be used in coordinating care of a user between one or more caregivers. CCSP system 100 may include a care coordination support platform ("CCSP") computing device 102. In the exemplary embodiment, CCSP computing device 102 is in communication with client devices 104, a chatbot server 106, and a sensor server 108. CCSP computing device 102 is also in communication with a database 118 and may communicate with database 118 through a database server 116.

In some embodiments, database server 116 is a component of CCSP computing device 102. In other embodiments, database server 116 is separate from CCSP computing device 102. Further, in some embodiments, chatbot server 106 is a component of CCSP computing device 102. In other embodiments, chatbot server 106 is separate from CCSP computing device 102. In some embodiments, CCSP system 100 may include a plurality of CCSP computing devices 102, client devices 104, chatbot servers 106, sensor servers 108, and/or databases 118.

In the exemplary embodiment, CCSP computing device 102 may be configured to store user and caregiver data and generate care schedules corresponding to the user and the caregivers. CCSP computing device 102 may receive user and caregiver data from client devices 104 and use the user and caregiver data to register users and caregivers and generate care schedules for the user and caregivers. For example, a user and a caregiver may download a CCSP application 110 to a device (e.g., client device 104) and input data into CCSP application 110 for registration with a service provided by CCSP computing device 102. The user and caregivers may also access a website of CCSP system 100 using a web browser, and input user data into the website to register with CCSP system 100.

The user data may include personal data (e.g., name, birthdate, height, weight, etc.), user tasks (e.g., taking medicine, bathing, eating, paying bills, getting groceries, car maintenance, home maintenance, etc.), user activities (e.g., social activities, like bingo and golfing, physical activities, like working out and keeping active, etc.), user appointments (e.g., recurring appointments like yearly physicals and bimonthly haircuts, etc.), and any other information associated with the user that may be useful to CCSP computing device 102.

The caregiver data may include personal information (e.g., name, contact information, relationship to the user, role in caring for the user, etc.), caregiver schedule information (e.g., known work and/or activity schedules of the caregivers), caregiver preferences (e.g., which events the caregiver prefers to assist the user with and/or how often the caregiver prefers to assist the user for any period of time, like no more than three hours a week or 8 hours a month), and any other information associated with the caregivers that may be useful to CCSP computing device 102.

CCSP application 110 may also receive other data from the user and caregivers including alert preferences of the user and caregivers (e.g., preferences of when the user and caregivers would like to be notified and how the user and caregivers would like to be notified, such as receiving a text notification and/or a push button notification from CCSP application 110).

In the exemplary embodiment, users and caregivers may update the user and caregiver data at any time through CCSP application 110. For example, user data that may need to be updated may include a change in and/or newly scheduled events of the user, and a change in a daily medication schedule of the user. For example, caregiver data that may need to be updated may include a change in and/or a new availability schedule of the caregiver, a new activity scheduled by the caregiver, and a vacation scheduled by the caregiver.

CCSP application 110 may be in communication with other applications of client device 104 and may import user and caregiver data from the other applications. For example, caregivers may allow CCSP application 110 to retrieve data from a calendar application of the caregivers such that the caregivers may only need to update the schedule associated with the caregiver in one application (e.g., a calendar application).

In the exemplary embodiment, CCSP computing device 102 may be configured to process all of the user and caregiver data CCSP computing device 102 receives from the user and caregivers (e.g., through CCSP application 110) and coordinate a care schedule of the user between the caregivers. CCSP computing device 102 may automatically assign each task, activity, and/or appointment of the user to the caregivers based upon the received caregiver data. For example, four caregivers may be associated with a user. A first caregiver, who is also an admin caregiver, may be a child of the user who works a full-time job and has three children with busy schedules, a second caregiver may be a child of the user who works part-time and does not have any children, a third caregiver may be a hired caregiver who spends up to 20 hours per week caring for the user, and a fourth caregiver may be a friend of the user who enjoys spending time with the user.

CCSP computing device 102 may process the caregiver data associated with each of the four caregivers and compare the caregiver data to the task, activity, and appointment schedule of the user. Based upon the compared data, CCSP computing device 102 may assign each task, activity, and appointment of the user to each of the caregivers and create a dynamic care schedule of the user. The admin caregiver may instruct CCSP computing device 102 (e.g., through CCSP application 110) to assign events to the third caregiver first before assigning the events to the admin caregiver and the second and fourth caregivers. Accordingly, CCSP computing device 102 may first assign the events of the user to the third caregiver, based upon the caregiver data of the third caregiver, before assigning the tasks to the admin, second, and fourth caregivers, based upon the caregiver data of the admin, second, and fourth caregivers.

If any of the caregiver data changes (e.g., one of the caregivers has a last-minute appointment or emergency), the caregiver may notify CCSP computing device 102, and CCSP computing device 102 may automatically assign the previously assigned task, activity, and/or appointment to another caregiver based upon the caregiver data of the other caregivers. Accordingly, CCSP computing device 102 may reduce friction in, and time spent, coordinating care of the user between caregivers by automatically assigning the care schedule of the user to the caregivers based upon caregiver data.

When CCSP computing device 102 receives user events, CCSP computing device 102 may further be configured to determine whether each of the events are critical or non-critical. For example, CCSP computing device 102 may determine whether the events are critical or non-critical based upon a description of the task, activity, and/or appointment and/or whether the user and/or caregiver specifically marks the task, activity, and/or appointment as critical or non-critical when inputting the task, activity, and/or appointment into CCSP application 110. For example, if a description of the task, activity, and/or appointment is "doctor's appointment," "take medicine," and/or "help user out of bed," CCSP computing device 102 may automatically determine that the task, activity, and/or appointment of the user is critical. However, if a description of the task, activity, and/or appointment is, for example, "Take user to bingo," "Mow grass of user," and/or "Get user's oil changed," CCSP computing device 102 may automatically determine that the task, activity, and/or appointment is non-critical.

In the exemplary embodiment, CCSP computing device 102 may receive data from sensor servers 108 that are associated with sensors and may use the data to coordinate care of a user and/or determine whether assigned events of the user have been carried out. Sensor servers 108 may include smart home device servers (e.g., AMAZON and GOOGLE servers), wearable device servers (e.g., FITBIT AND APPLE servers), vehicle telematics device servers, home telematics device servers, and smart device servers. Data from the sensors may include interaction data from a smart home device (e.g., AMAZON ALEXA, GOOGLE HOME, and/or RING doorbells), activity and/or location data from a wearable device (e.g., FITBIT and APPLE WATCH), driving data and/or location data from autonomous or semi-autonomous vehicles smart vehicle sensors, and daily medication taking from a smart pillbox sensor.

Further, CCSP computing device 102 may receive sensor data (e.g., GPS location) from sensors of client devices 104. CCSP computing device 102 and sensor servers 108 may be communicatively coupled through any suitable connection including through the Internet through many interfaces including, but not limited to, at least one of a network, such as the Internet, a local area network (LAN), a wide area network (WAN), or an integrated services digital network (ISDN), a dial-up-connection, a digital subscriber line (DSL), a cellular phone connection, and a cable modem.

CCSP computing device 102 may be configured to determine whether an assigned event of the user has been carried out by the user and/or the caregiver. For example, if a caregiver was assigned with bringing the user dinner on a certain day, CCSP computing device 102 may use RING doorbell data of the user and/or location data of the caregiver to determine if the caregiver brought the user dinner. For another example, if a user is assigned with taking medicine three times a day at specific time intervals, CCSP computing device 102 may use smart pillbox data to determine if a pillbox of the user was opened at the specific time intervals. If CCSP computing device 102 determines that a task, activity, and/or appointment has not been carried out, CCSP computing device 102 may alert (e.g., through CCSP application 110) the user and/or caregivers based upon the user and caregiver data (e.g., alert preferences). In some embodiments, in determining whether an event of the user has been carried out, CCSP computing device 102 may receive and/or retrieve location and time data from the event. CCSP computing device 102 may be configured to monitor and/or collect location and time data from the user (e.g., through time-stamped GPS and/or geofence location data from a mobile device, wearable device, or any other suitable device associated with the user). CCSP computing device 102 may compare the received location and time data for the event with the location and time data of the user during the event. If the received location and time data and the user location and time data are the same, CCSP computing device 102 may determine that the event was carried out. If the received location and time data and the location and time data of the user are not the same, CCSP computing device 102 may determine that the event was not carried out.

In some embodiments, CCSP computing device 102 may be configured to display (e.g., through CCSP application 110) the generated care schedule to the user and/or caregivers. CCSP computing device 102 may display the generated care schedule to the user and caregivers through task lists, graphs, calendars, and any other suitable interface that allows the user and caregiver to easily take in and interact with the care schedule of the user.

Further, CCSP computing device 102 may be configured to generate and display (e.g., through CCSP application 110) caregiver analytics of each caregiver based upon the care schedule of the user. For example, CCSP computing device 102 may create graphs of time each caregiver spends caring for the user, time each caregiver spends scheduling and/or participating in the scheduling of care for the user, and a task distribution of the percentage of events assigned to and carried out by each user over a predetermined period of time (e.g., a week, a month, and a year).

In the exemplary embodiment, CCSP computing device 102 may be in communication with chatbot server 106 associated with a chatbot. The chatbot may be any suitable chatbot and/or robo-assist device that functions as described herein. The chatbot may assist the user and caregivers (e.g., through CCSP application 110) in adding, editing, and/or deleting user and caregiver data, receiving information about the assigned care schedule, and/or receiving information about how the user and caregivers are carrying out the care schedule.

For example, instead of a user and/or caregiver having to manually input (e.g., using a structured command format or menu) each task, activity, and appointment of the user, each notification request of the user and caregivers, and/or each schedule item of the caregivers, the user and caregivers may give instructions to the chatbot (e.g., through typing and/or speaking plain-language commands and/or questions into the chatbot through CCSP application 110). Also, for example, if the user just made an appointment, the user may instruct the chatbot using natural language to add the appointment to the user's calendar and assign the appointment to one of the caregivers. Further, a caregiver may instruct the chatbot to remind the caregiver to pay the user's bills ever month.

The user and caregivers may also ask the chatbot questions. For example, the user may ask the chatbot who is taking them to Bingo on a particular day, and the caregiver may ask the chatbot to identify the last time the user took their medicine. The chatbot may also notify and/or send alerts to the user and caregivers based upon the user and caregiver alert preferences. Also, for example, the chatbot may notify a caregiver that a user has not yet taken their medicine, and the chatbot may ask the caregiver if the caregiver would like the chatbot to send a reminder to the user to take their medicine. If the caregiver says yes, the chatbot may automatically cause the CCSP computing device 102 to send the reminder to the user.

Further, chatbot server 106, along with CCSP computing device 102, may be configured to use machine learning algorithms and/or programs to learn from the user and/or caregivers, as described herein. For example, CCSP computing device 102 may receive task monitoring and/or completion data generated by sensor servers 108 based upon a task being completed by the user and/or the assigned caregiver. Although described as implemented on chatbot server 106 separate from CCSP computing device 102, the chatbot may alternatively be co-implemented on CCSP computing device 102.

In the exemplary embodiment, client devices 104 may be computers that include a web browser or a software application, which enables client devices 104 to access remote computer devices, such as CCSP computing device 102, using the Internet or other network. More specifically, client devices 104 may be communicatively coupled to the Internet through many interfaces including, but not limited to, at least one of a network, such as the Internet, a local area network (LAN), a wide area network (WAN), or an integrated services digital network (ISDN), a dial-up-connection, a digital subscriber line (DSL), a cellular phone connection, and a cable modem. Client devices 104 may be any device capable of accessing the Internet including, but not limited to, a desktop computer, a laptop computer, a personal digital assistant (PDA), a cellular phone, a smartphone, a tablet, a phablet, wearable electronics, smart watch, or other web-based connectable equipment or mobile devices. Further, CCSP computing device 102 may be communicatively coupled to client devices 104 and may receive information from client devices 104.

Database server 116 may be communicatively coupled to database 118 that stores data. In one embodiment, database 118 may include user data, caregiver data, sensor data, mobile device data, assignment data, and notification data. In the exemplary embodiment, database 118 may be stored remotely from CCSP computing device 102. In some embodiments, database 118 may be decentralized. In the exemplary embodiment, a user and/or caregiver, may access database 118 via their respective client devices 104 by logging onto CCSP computing device 102, as described herein.

In the exemplary embodiment, client devices 104 include CCSP application 110 and a user interface 112. User interface 112 may be used, for example, to receive notifications from CCSP computing device 102 and/or to input and verify information to be sent to CCSP computing device 102. CCSP application 110 may be, for example, a program or application that runs on client device 104.

Exemplary User Computer Device

Figure 2:
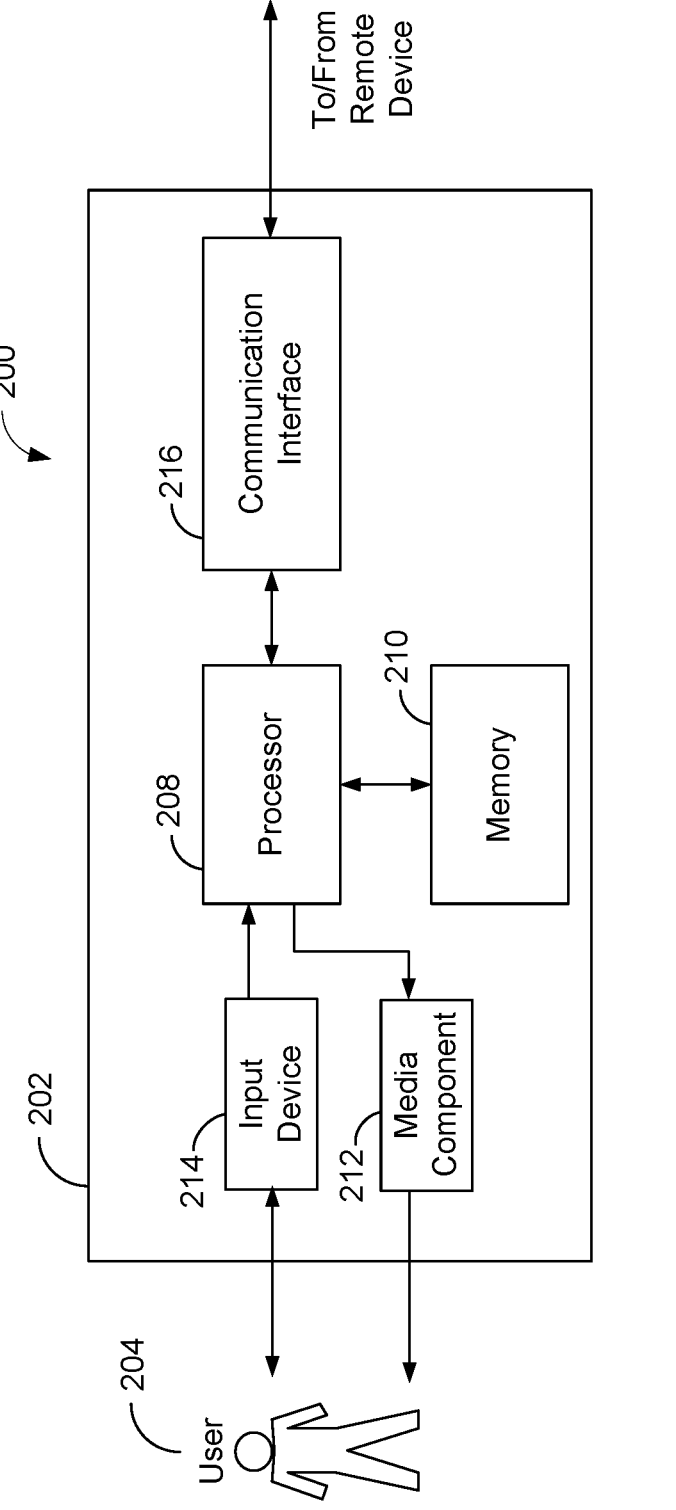
FIG. 2 illustrates an exemplary configuration of an exemplary user computing device that may be used in the care coordination support computer system illustrated in FIG. 1.

FIG. 2 illustrates an exemplary configuration 200 of an exemplary user computing device 202. In some embodiments, user computing device 202 may be in communication with a care coordination support platform computing device (such as CCSP computing device 102, shown in FIG. 1). User computing device 202 may be representative of, but is not limited to client devices 104 and/or sensor servers 108. For example, user computing device 202 may be a mobile device, smartphone, tablet, smartwatch, wearable electronic, laptop, desktop, or another type of computing device associated with an account holder (e.g., the user and/or the associated caregivers).

User computer device 202 may be operated by a user 204 (e.g., a user of CCSP system 100, shown in FIG. 1 and substantially similar to the user and/or the caregivers described herein). User computer device 202 may receive input from user 204 via an input device 214. User computer device 202 includes a processor 208 for executing instructions. In some embodiments, executable instructions may be stored in a memory area 210. Processor 208 may include one or more processing units (e.g., in a multi-core configuration)

. Memory area 210 may be any device allowing information such as executable instructions and/or user and registration data to be stored and retrieved. Memory area 210 may include one or more computer-readable media.

User computer device 202 also may include at least one media output component 212 for presenting information to user 204. Media output component 212 may be any component capable of conveying information to user 204 and may be used to at least partially implement user interface 112 (shown in FIG. 1). In some embodiments, media output component 212 may include an output adapter (not shown), such as a video adapter and/or an audio adapter. An output adapter may be operatively coupled to processor 208 and operatively coupleable to an output device, such as a display device (e.g., a cathode ray tube (CRT), liquid crystal display (LCD), light emitting diode (LED) display, or "electronic ink" display) or an audio output device (e.g., a speaker or headphones).

In some embodiments, media output component 212 may be configured to present a graphical user interface (e.g., a web browser and/or a client application) to user 204. A graphical user interface may include, for example, care calendars for the user and/or associated caregivers, notifications for the user and/or associated caregivers, assigned tasks of the caregivers, an activity analytics of the caregivers, and/or a messaging page for interacting with a chatbot (e.g., the chatbot associated with chatbot server 106 shown in FIG. 1).

In some embodiments, user computer device 202 may include input device 214 for receiving input from user 204. User 204 may use input device 214 to, without limitation, interact with CCSP system 100 (e.g., using CCSP application 110), CCSP computing device 102, or any of client devices 104, chatbot servers 106, and sensor servers 108 (shown in FIG. 1). Input device 214 may include, for example, a keyboard, a pointing device, a mouse, a stylus, and/or a touch sensitive panel (e.g., a touch pad or a touch screen) and may be used to at least partially implement user interface 112 (shown in FIG. 1). A single component, such as a touch screen, may function as both an output device of media output component 212 and input device 214. User computer device 202 may further include at least one sensor, including, for example, a gyroscope, an accelerometer, a position detector, a biometric input device, and/or an audio input device. In some embodiments, at least some data collected by user computer device 202 may be transmitted to CCSP computing device 102. In the exemplary embodiment, data collected by user computer device 202 may be included in user and caregiver data.

User computer device 202 may also include a communication interface 216, communicatively coupled to any of CCSP computing device 102, client devices 104, chatbot servers 106, and sensor servers 108. Communication interface 216 may include, for example, a wired or wireless network adapter and/or a wireless data transceiver for use with a mobile telecommunications network.

Stored in memory area 210 may be, for example, computer-readable instructions for providing a user interface to user 204 via media output component 212 and, optionally, receiving and processing input from input device 214. The user interface may include, among other possibilities, a web browser and/or a client application. Web browsers enable users, such as user 204, to display and interact with media and other information typically embedded on a web page, a website, or an application hosted by CCSP computing device 102 and/or client device 104. A client application may allow user 204 to interact with, for example, any of CCSP computing device 102, client devices 104, chatbot servers 106, and sensor servers 108. For example, instructions may be stored by a cloud service and the output of the execution of the instructions sent to the media output component 212. User computing device 200 may include additional, less, or alternate functionality, including that discussed elsewhere herein.

Exemplary Server Device

Figure 3:
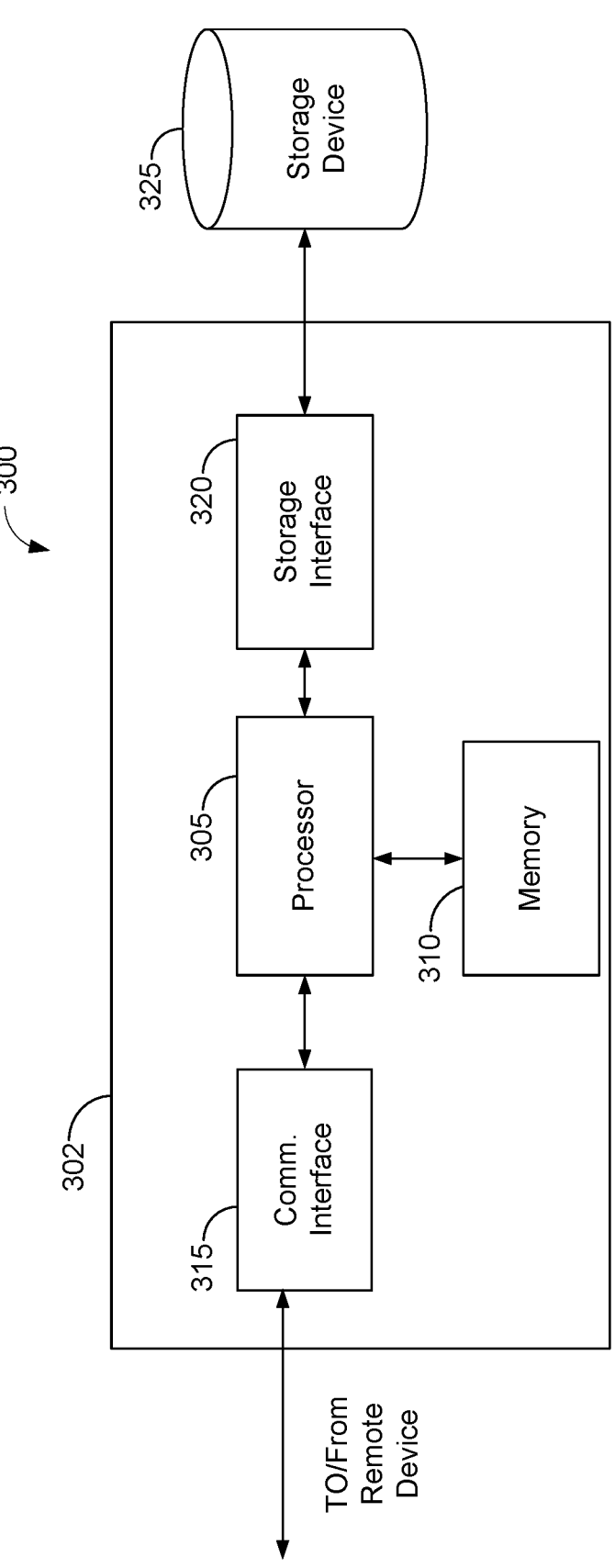
FIG. 3 illustrates an exemplary configuration of an exemplary server computing device that may be used in the care coordination support computer system illustrated in FIG. 1.

FIG. 3 depicts an exemplary configuration 300 of an exemplary server computer device 302, in accordance with one embodiment of the present disclosure. Server computer device 302 may include, but is not limited to, CCSP computing device 102 (shown in FIG. 1) and/or chatbot server 106 (shown in FIG. 1). Server computer device 302 may include a processor 305 for executing instructions. Instructions may be stored in a memory area 310. Processor 305 may include one or more processing units (e.g., in a multi-core configuration).

Processor 305 may be operatively coupled to a communication interface 315 such that server computer device 302 may be capable of communicating with a remote device such as another server computer device 302 or a user computing device, such as client device 104 (shown in FIG. 1). For example, communication interface 315 may receive requests from or transmit requests to client devices 104 via the Internet.

Processor 305 may also be operatively coupled to a storage device 325. Storage device 325 may be any computer-operated hardware suitable for storing and/or retrieving data, such as, but not limited to, data associated with database 118 (shown in FIG. 1). In some embodiments, storage device 325 may be integrated in server computer device 302. For example, server computer device 302 may include one or more hard disk drives as storage device 325. In other embodiments, storage device 325 may be external to server computer device 302 and may be accessed by a plurality of server computer devices 302. For example, storage device 325 may include a storage area network (SAN), a network attached storage (NAS) system, and/or multiple storage units such as hard disks and/or solid state disks in a redundant array of inexpensive disks (RAID) configuration.

In some embodiments, processor 305 may be operatively coupled to storage device 325 via a storage interface 320. Storage interface 320 may be any component capable of providing processor 305 with access to storage device 325. Storage interface 320 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 305 with access to storage device 320.

Processor 305 executes computer-executable instructions for implementing aspects of the disclosure. In some embodiments, processor 305 may be transformed into a special purpose microprocessor by executing computer-executable instructions or by otherwise being programmed.

Exemplary Computer-Implemented Method

Figure 4:
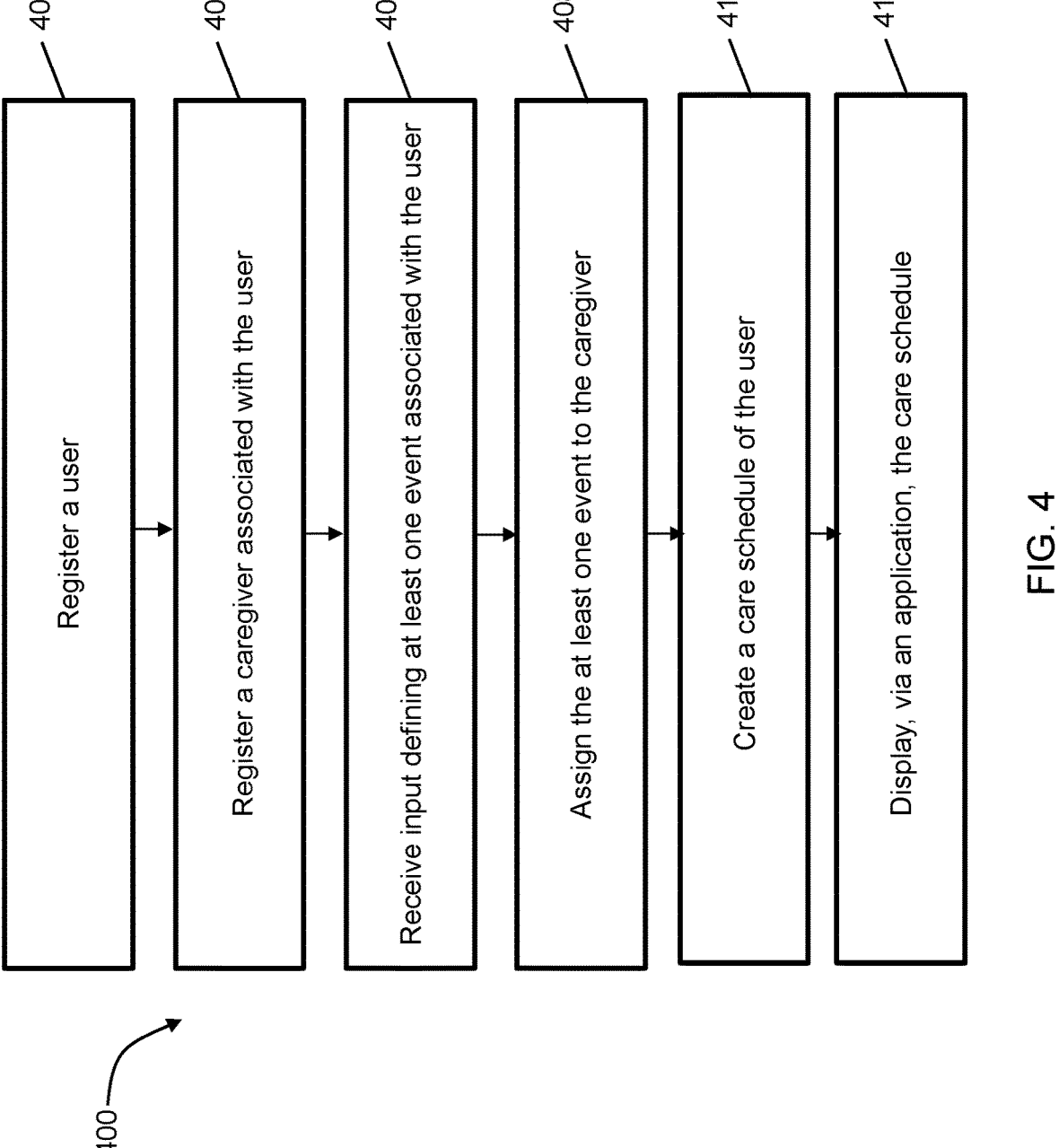
FIG. 4 illustrates a flow chart of an exemplary computer-implemented method implemented by the exemplary care coordination support computer system shown in FIG. 1.

FIG. 4 depicts a flow chart illustrating a computer-implemented method 400 for coordinating care between caregivers associated with a user. In the exemplary embodiment, method 400 may be implemented by a care coordination support platform computer system such as CCSP computing device 102 (shown in FIG. 1).

Method 400 may include registering 402 a user and registering 404 at least one caregiver associated with the user for a care coordination support platform service (e.g., provided by CCSP computer system shown in FIG. 1). Method 400 may also include receiving 406 at least one event associated with the user.

Method 400 may further include assigning 408 the at least one event to the at least one caregiver and creating 410 a care schedule of the user that includes the assigned 408 at least one event. Method 400 may further include displaying 410, via an application associated with CCSP computing device 102, shown in FIG. 1, the care schedule to the at least one caregiver.

Exemplary Computer Device

Figure 5:
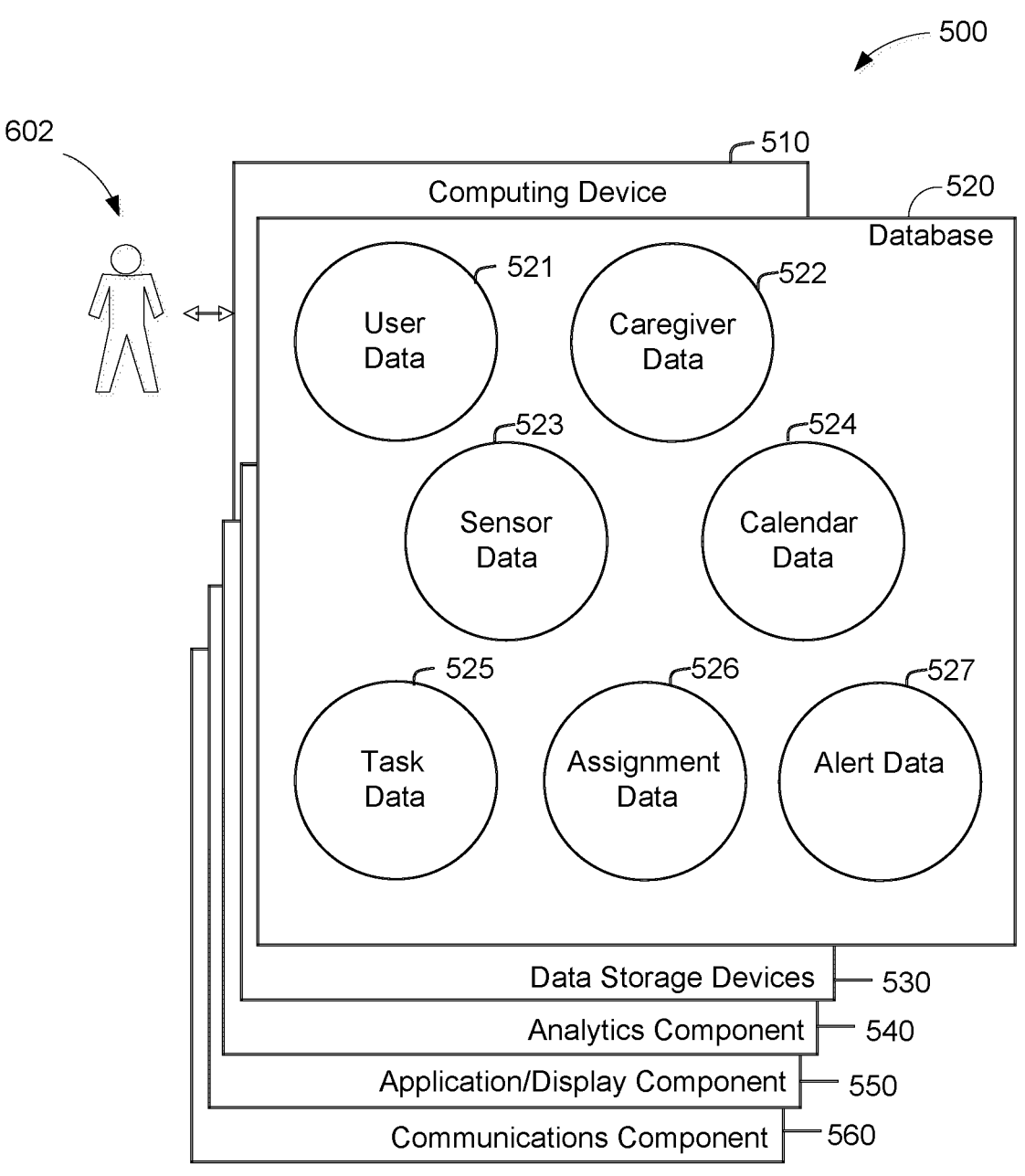
FIG. 5 illustrates a diagram of components of one or more exemplary computing devices that may be used in the care coordination support platform computer system shown in FIG. 1.

FIG. 5 depicts a diagram 500 of components of one or more exemplary computing devices 510 that may be used in care coordination support platform system 100 (shown in FIG. 1). In some embodiments, computing device 510 may be similar to CCSP computing device 102 (shown in FIG. 1). Database 520 may be coupled with several separate components within computing device 510, which perform specific tasks. In this embodiment, database 520 may include user data 521, caregiver data 522, sensor data 523, calendar data 524, task data 525, assignment data 526, and alert data 527. In some embodiments, database 520 is similar to database 118 (shown in FIG. 1).

Computing device 510 may include database 520, as well as data storage devices 530. Computing device 510 may also include an analytics component 540 for analyzing received user and caregiver data to assign events to caregivers based upon the received data. Computing device 510 may further include application/display component 550 for generating and displaying information to users, such as through CCSP application 110 (shown in FIG. 1), and supporting CCSP application 110. Moreover, computing device 510 may include communications component 560 for receiving and transmitting data (e.g., to and from user devices 104 and chatbot server 106), such as user data 521, caregiver data 522, sensor data 523, calendar data 524, task data 525, assignment data 526, and alert data 527. Computing devices 510 may include additional, less, or alternate functionality, including that discussed elsewhere herein.

Exemplary Care Coordination Support Application

FIGS. 6-20 include screenshots of one example embodiment of an application (e.g., CCSP application, shown in FIG. 1) executable as part of a care coordination support platform system (e.g., care coordination support platform system 100, shown in FIG. 1). The application may be accessible on any suitable electronic device, such as a mobile phone, tablet, watch, or any other computing device. The application enables a user to determine what tasks the users need to complete, view a care coordination schedule of the user, enables one or more caregivers to add tasks for the user, view the tasks that the one or more caregivers have to complete for and/or with the user, and coordinate the care schedule between the one or more caregivers.

In some embodiments, the application may enable the user and the one or more caregivers to subscribe to alerts, notifications, and/or reminders. Further, in some embodiments, the application may implement a chatbot that allows the user and/or the one or more caregivers to seamlessly add tasks, set reminders, and issue reminders based upon natural language instructions.

The application may be configured to communicate with various other software and/or applications on the computing devices of the users and/or the one or more caregivers. For example, the application may be able to access or otherwise communicate with calendar applications and/or contact applications. The application may be configured to retrieve data from and/or report data to these other applications. In addition, the application may be configured to track, monitor, and/or record application utilization metrics for the user and/or the caregivers, such as how often the user and/or the caregivers access the application, and the various features of the application used by the user and/or the caregivers.

In one embodiment, the application, once downloaded onto the computing device of the user and/or the caregivers, may not require internet connectivity to perform some or all of the functionality of the application (e.g., setting alerts and notifying the user and/or caregivers of the alerts). In some embodiments, all or a portion of the data input by the user and/or caregivers into the application (including, for example, application utilization metrics, task logs, etc.) may be electronically transmitted to a server (e.g., CCSP server 102) for processing, and the processed data may be transmitted back for further processing and/or display by the application.

Figures 6, 7:
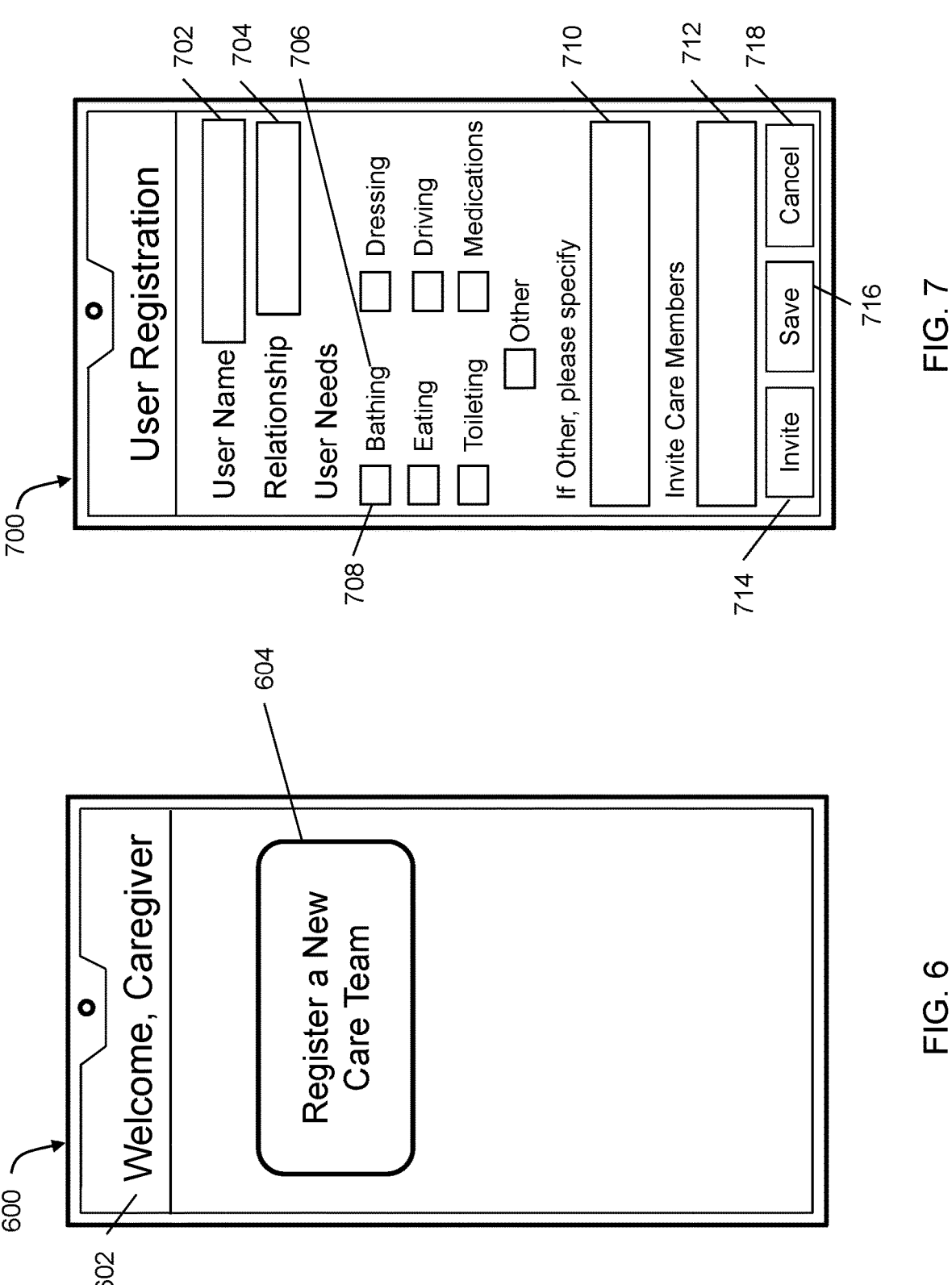

FIG. 6 illustrates an initial welcome page 600 that may include a header 602. Although not specifically shown, header 602 may include a home button, a back button, and any other buttons to help the user and/or the caregivers navigate the application. In some embodiments, initial welcome page 600 may further include a footer (not specifically shown) that may include additional buttons to help the user and/or the caregiver navigate the application. Initial welcome screen 600 may also include a "Register a New Care Team" button 604 that, when clicked, may cause the application to display a user registration screen 700.

FIG. 7 illustrates user registration page 700 for the application. User registration page 700 may include a first field 702 for the user and/or an administrative caregiver (e.g., "admin caregiver") to enter the name of the user and a second field 704 to, if user registration page 700 is filled out by the admin caregiver, enter the relationship of the admin caregiver to the user.

Further, user registration page 700 may include certain user needs 706, and each user need 706 may be accompanied by a corresponding check box 708 that the user and/or admin caregiver may check if the user has the corresponding user need 706. For example, if the user has a "bathing" need 706, the user and/or admin caregiver may check check box 708 that corresponds to the "bathing" need 706.

User registration page 700 may further include a third field 710 for the user and/or admin caregiver to fill in additional needs that the user may have that are not spelled out in user needs 706. Further, user registration page 700 may include a fourth field 712 for the user and/or admin caregiver to enter email addresses, phone numbers, and/or other contact information of other caregivers such that the application may invite the other caregivers to download the application.

User registration page may include an "Invite" button 714, that, when clicked, may cause the application to invite the other caregivers to download the application and/or show a caregiver registration page 800, a "Save" button 716 that, when clicked, may cause the application to save the information in fields 702, 704, 710, and 712, and a "Cancel" button 718 that, when clicked may cause the application to go back to initial welcome page 600. Once other caregivers download the application, the other caregivers may be directly navigated to caregiver registration page 800 and may bypass initial welcome page 600 and/or user registration page 700.

Figure 8:
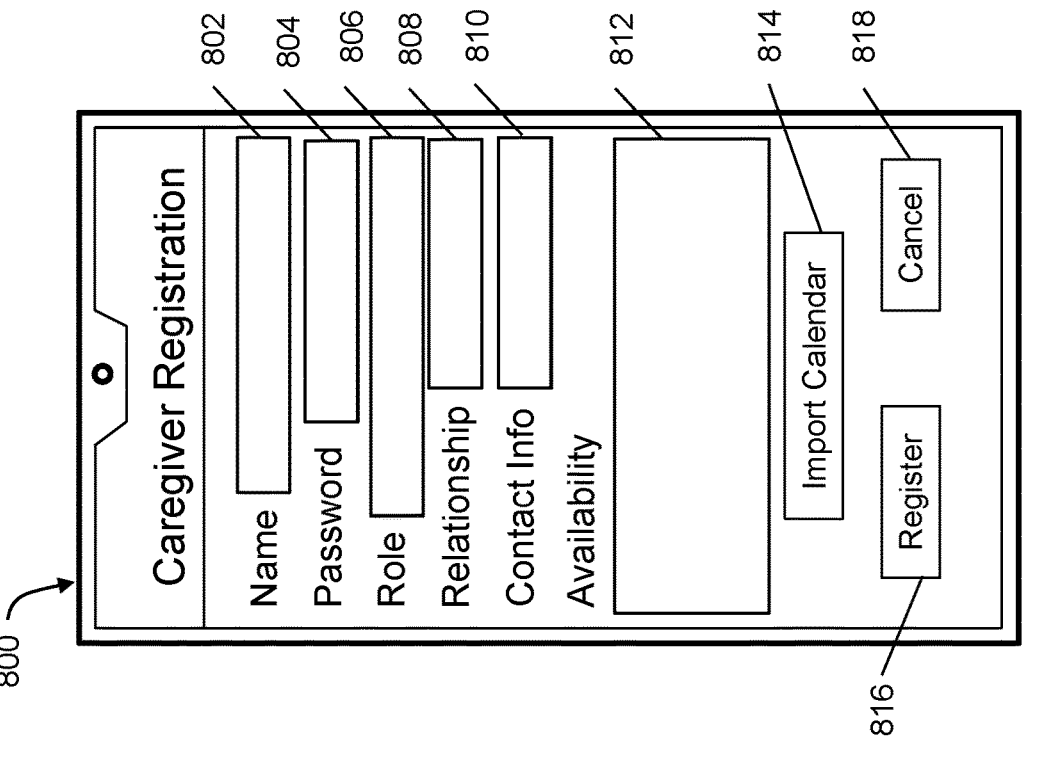

FIG. 8 illustrates caregiver registration page 800 for the application that allows the admin caregiver and/or the other caregivers to register for the application. Caregiver registration page 800 may include a first field 802 for the caregiver to enter the name of the caregiver, a second field 804 for the caregiver to enter a password for the application, a third field 806 for the caregiver to enter a role that the caregiver carries out in caring for the user, a fourth field 808 for the caregiver to enter a relationship of the caregiver to the user, and a fifth field 810 for the caregiver to enter contact information (e.g., phone number(s), email address, and/or home address).

Further, caregiver registration page 800 may include a sixth field 812 for the caregiver to enter availability (e.g., work schedule and/or calendar schedule) of the caregiver. The availability of the caregiver may be manually entered into the sixth field 812 and/or the caregiver may click an "Import Calendar" button 814 that, when clicked, may cause the application to access calendar data of the user and automatically populate sixth field 812. Caregiver registration page 800 may further include a "Register" button 816 that, when clicked, may cause the application to save and store the information that caregiver entered into fields 802, 804, 806, 808, 810, and/or 812, and display a welcome screen 900, and caregiver registration page 800 may include a "Cancel" button 818 that, when clicked, may cause the application to close and show a different screen (e.g., a home screen) of the device running the application.

Figure 9:
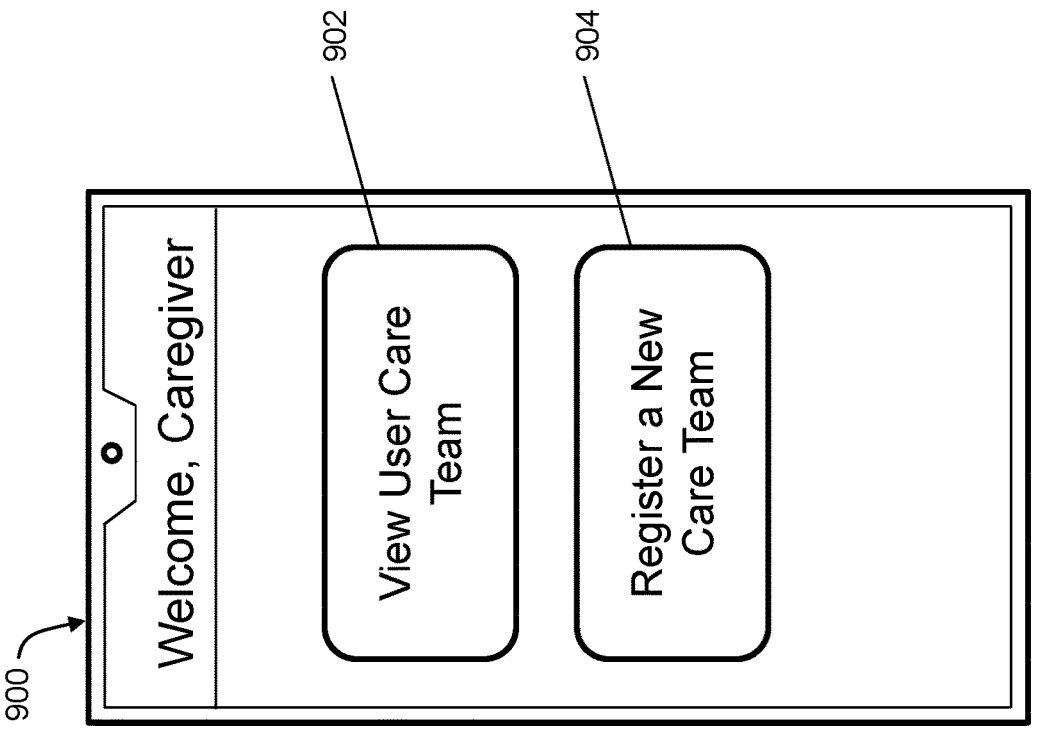

FIG. 9 illustrates welcome page 900 that may be the first page that the user and/or the admin caregiver are directed to until a user care team is complete (e.g., the user and all caregivers associated with the user are registered through the application). Welcome page 900 may include a "View User Care Team" button 902 that, when pressed, may cause the application to display a user care team page 1000 and a "Register New Care Team" button 904, when pressed, may cause the application to display user registration page 700.

Figure 10:
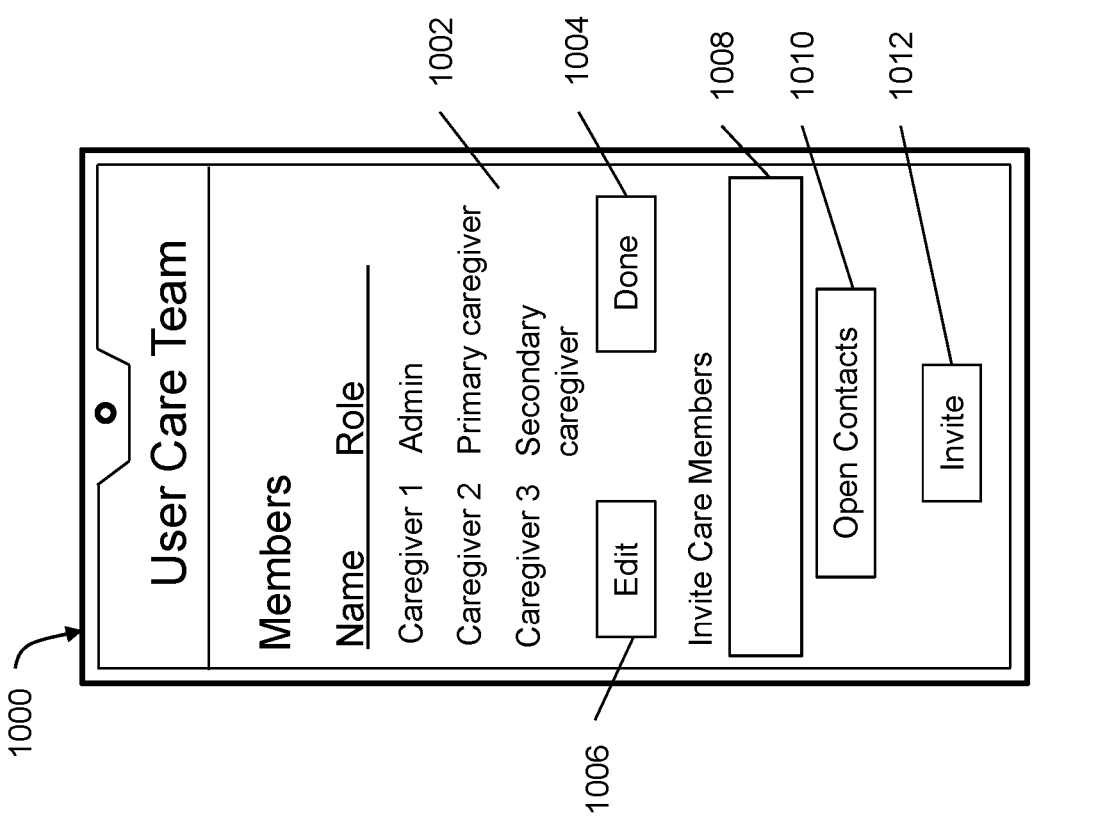

FIG. 10 illustrates user care team page 1000 that may allow the user and/or the admin caregiver to view and/or edit the care team associated with the user. User care team page 1000 may include a list 1002 of registered members of the care team including the names of the caregivers (e.g., entered by the caregivers in first field 802 of caregiver registration page 800, shown in FIG. 8) and roles of the caregivers (e.g., entered by the caregivers in third field 806 of caregiver registration page 800, shown in FIG. 8).

User care team page 1000 may also include an "Edit" button 1006 that, when clicked, allows the user and/or admin caregiver to edit list 1002 and a "Done" button 1004 that, when clicked, causes the application to save the care team and store the care team as fully registered. User care team page 1000 may also include a first field 1008 where the user and/or the admin caregiver may manually enter contact information of additional caregivers to add to the care team.

Additionally or alternatively, the user and/or the admin caregiver may press a "Open Contacts" button 1010 that, when pressed, causes the application to open the contacts of the user and/or admin caregiver and allow the user and/or admin caregiver to automatically choose which contacts the user and/or admin caregiver would like to invite to the care team. When the user and/or admin caregiver is done adding contact information of additional caregivers, the user and/or admin caregiver may press an "Invite" button 1012 that, when clicked, causes the application to invite the additional caregivers to register for the application.

Figures 11, 12:
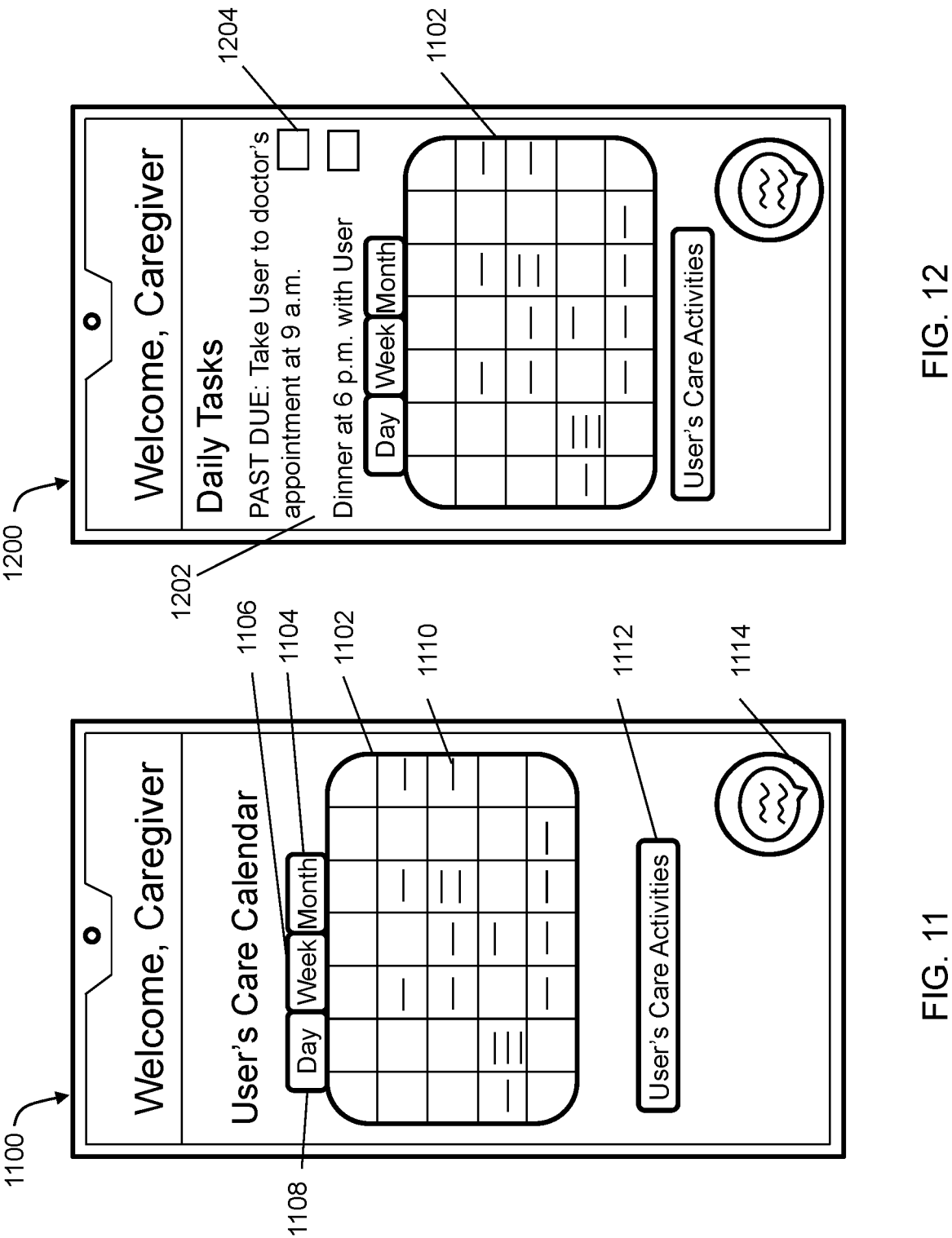

FIG. 11 shows an example caregiver planner page 1100 that the user and/or caregivers may be directed to when the user and/or caregivers open the application after the user and/or caregivers have been registered for the application. Caregiver planner page 1100 may include a care calendar 1102 of the user. In the example embodiment, care calendar 1102 is shown in a monthly view.

Additionally or alternatively, the user and/or caregivers may change care calendar 1102 view by clicking on a month button 1104 that, when clicked, shows care calendar 1102 in a monthly view, a week button 1106 that, when clicked, shows care calendar 1102 in a weekly view, and a day button 1108 that, when clicked, shows care calendar 1102 in a daily view. Care calendar 1102 may include lines 1110 that indicate to the user and/or caregivers when a task, activity, and/or appointment is scheduled for the user. For example, lines 1110 may indicate that the caregiver using the application has assigned events to take care of for and/or with the user on specific dates of care calendar 1102, or lines 1110 may indicate that the user has assigned events on specific dates of care calendar 1102, and lines 1110 may not be specific to one caregiver.

Further, caregiver planner page 1100 may include a "User's Care Activities" button 1112 that, when clicked, may cause the application to display user's care activities page 1900. Caregiver planner page 1100 may also include a chatbot button 1114 that, when clicked, causes the application to open a chatbot messaging page, examples of which are shown in a first, a second, a third, and a fourth chatbot messaging page 1400, 1500, 1600, 1700, and 1800.

FIG. 12 illustrates another example of a caregiver planner page 1200. Caregiver planner page 1200 is substantially similar to caregiver planner page 1100 (shown in FIG. 11). However, caregiver planner page 1200 shows to the caregiver using the application their daily assigned tasks 1202 above care calendar 1102. Daily assigned tasks 1202 may be accompanied by check boxes 1204. The caregiver may manually check check boxes 1204, or cause them to be checked by instructing the chatbot, when the accompanying daily task 1202 is completed by the caregiver, and/or the application may automatically check check boxes 1204 after the application determines that the accompanying daily task 1202 is completed by the caregiver and/or user (e.g., via sensor data and/or mobile device data, as described above).

Figures 13, 14, 15:
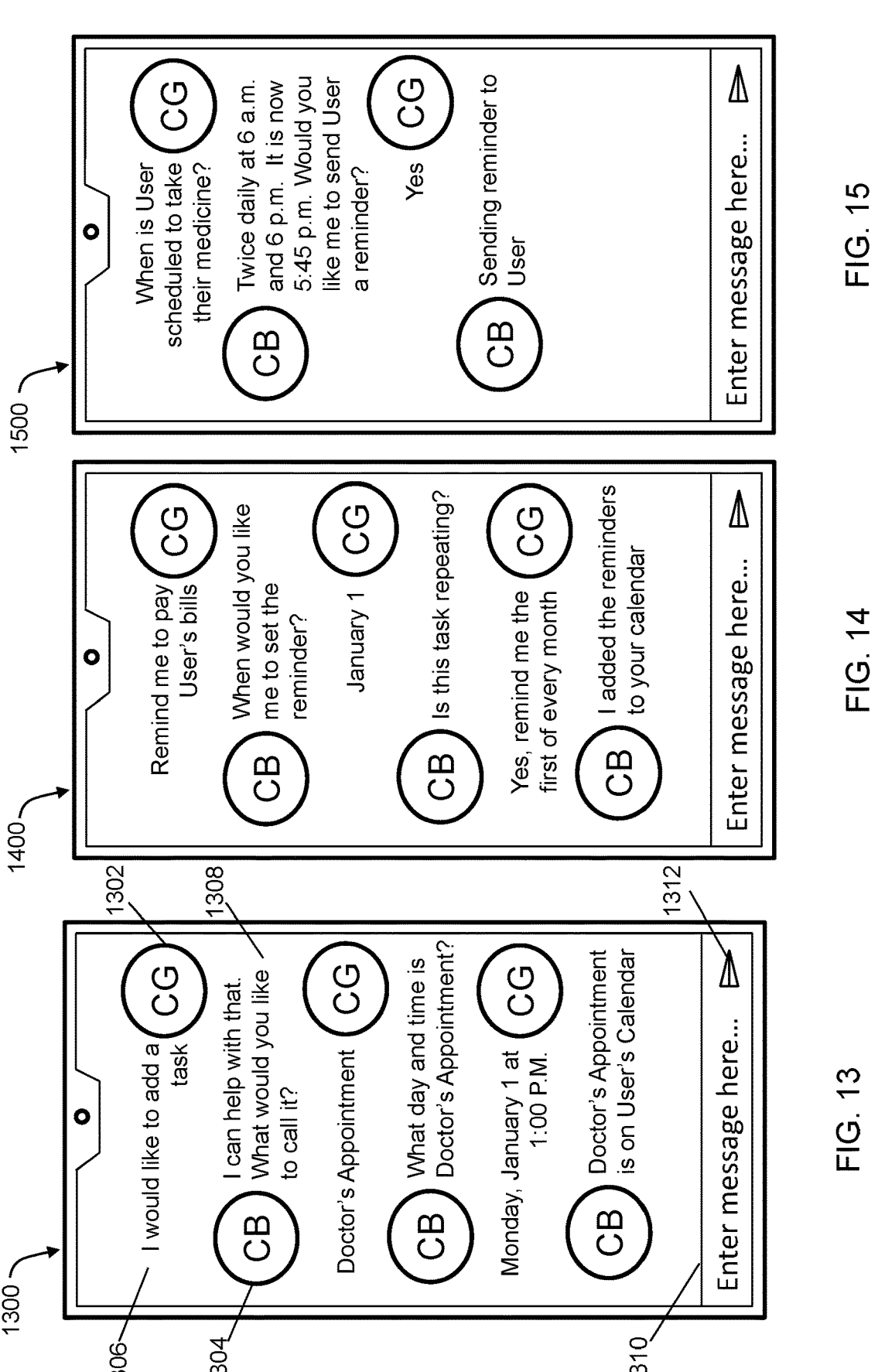

FIG. 13 illustrates first chatbot messaging page 1300. First chatbot messaging page 1300 page may include a first icon 1302 for caregiver messages 1306 and a second icon 1304 for chatbot messages 1308. In the exemplary embodiment, chatbot messaging page 1300 includes a first message field 1310 where the user and/or caregivers may enter messages for a chatbot (e.g., chatbot 106, shown in FIG. 1) and a send icon 1312 that, when clicked, may cause the application to send the entered message to the chatbot.

In other embodiments, messages may be entered into the chatbot through the user and/or caregiver speaking into a microphone of the device associated with the user and/or caregiver, or through any other suitable media such that the chatbot can receive and interpret the messages. Chatbot messaging page 1300 shows the caregiver asking the chatbot to add an appointment to the user's calendar (e.g., care calendar 1102 shown in FIG. 1). Further, chatbot messaging page 1300 shows a conversation between a caregiver and the chatbot. In other embodiments, multiple caregivers and/or the user may be involved in the conversation with the chatbot.

FIGS. 14, 15, 16, 17, and 18 illustrate second, third, fourth, fifth, and sixth chatbot messaging pages 1400, 1500, 1600, 1700, and 1800. Chatbot messaging pages 1400, 1500, 1600, 1700, and 1800 are substantially similar to first chatbot messaging page 1300 (shown in FIG. 13) and are illustrated to shown more capabilities of the chatbot. For example, chatbot messaging page 1400 shows the chatbot setting reminders for the caregiver to pay the user's bills, chatbot messaging page 1500 shows the chatbot answering the caregiver's question about when the user takes medicine and asking the caregiver if the chatbot needs to send a reminder to the user to take the medicine of the user, chatbot messaging page 1600 shows the chatbot notifying the caregiver that the user has not yet taken the medicine of the user at the scheduled time, chatbot messaging page 1700 shows the chatbot assisting two caregivers in coordinating and scheduling who is taking the user to doctor's appointments, and chatbot messaging page 1800 shows the chatbot assisting caregivers in determining who can take the user to dinner since the scheduled caregiver has a conflict.

Chatbot messaging pages 1400, 1500, 1600, 1700, and 1800 further show that the chatbot may learn and predict what the user and/or caregiver might ask the chatbot to do. For example, chatbot messaging page 1400 shows the chatbot asking the user if the reminder to pay the user's bills is a repeating task. Since bills are a task that must be completed frequently and since the caregiver asked the chatbot to set a reminder for the caregiver to pay bills, the chatbot may predict that the caregiver wants a frequent reminder to pay the bills. Further, chatbot messaging page 1800 shows that the first caregiver informs the chatbot and other caregivers that the first caregiver cannot take the user to dinner, and the second caregiver asks what time. The chatbot may predict that since the second caregiver asked the time, that the second caregiver is asking if the second caregiver would be able to take the user to dinner and may learn to check the second caregiver's schedule to determine if the second caregiver is busy. Accordingly, the chatbot may learn what the caregivers are asking and/or needing and answer the questions and/or fulfill the caregivers' needs without needing input from the caregivers.

Figure 19:
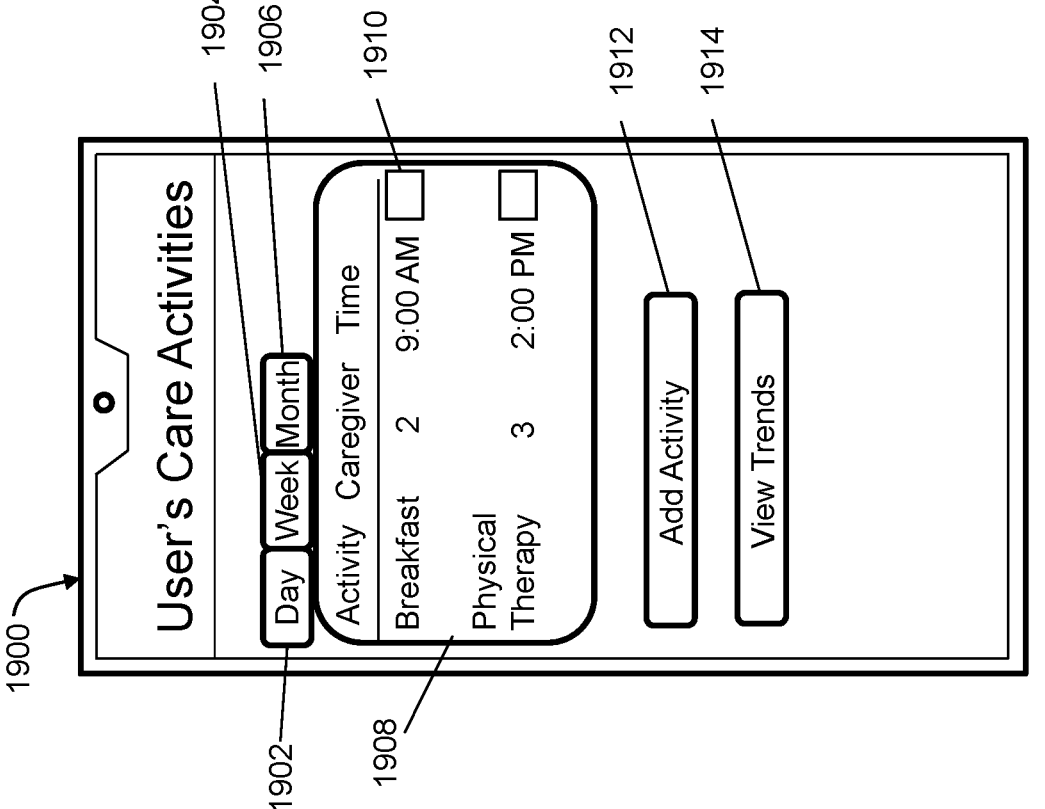

FIG. 19 illustrates user's care activities page 1900. User's care activities page 1900 may include a list 1908 of the user's scheduled activities along with the caretaker assigned to carry out the scheduled activity for and/or with the user and a time at which the user's activity is scheduled. List 1908 may be accompanied by check boxes 1910. The assigned caregiver, the user, and/or the admin caregiver may manually check, or may instruct the chatbot to check, the corresponding check box 1908 when the activity has been taken care of by the assigned caregiver and/or the application may automatically check the corresponding check box when the application determines that the activity has been taken care of, as described above.

List 1908 may be viewed by the user and/or caregivers on a daily basis (i.e., as a daily schedule) by clicking a day button 1902, on a weekly basis by clicking a week button 1904, and/or on a monthly basis by clicking a month button 1906. User's care activities page 1900 may further include an "Add Activity" button 1912 that, when clicked, allows the user and/or caregiver to manually add an activity or add an activity through the chat bot (e.g., via a chatbot messaging page 1400, 1500, 1600, 1700, and 1800, shown in FIGS. 13, 14, 15, 16, 17, and 18) and a "View Trends" button 1914 that, when clicked, may cause the application to display an activity trends page 2000.

Figure 20:
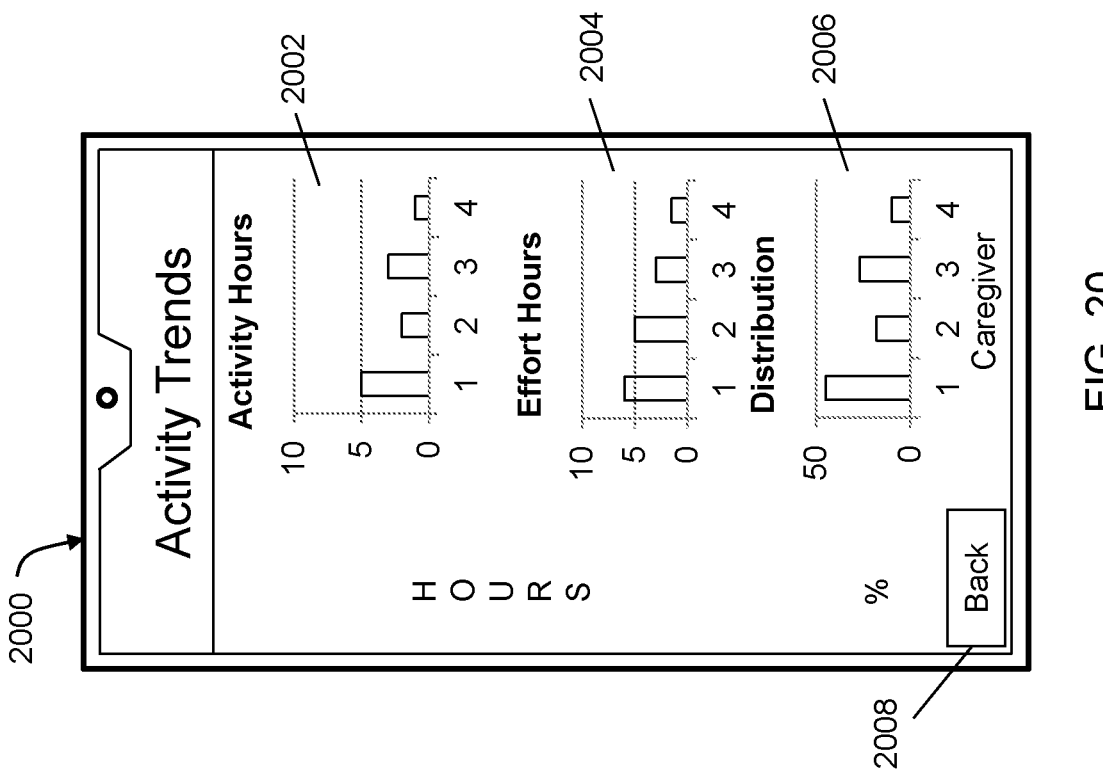

FIG. 20 illustrates activity trends page 2000. Activity trends page 2000 may include an activity hours chart 2002, an effort hours chart 2004, and/or a distribution chart 2006. Activity hours chart 2002 may display the amount of time that each caregiver spends carrying out activities for the user. Effort hours chart 2004 may display the amount of time that each caregiver spends putting in effort to the care of the user (e.g., checking and/or coordinating care, general time spent with the user when the caregiver is not scheduled, etc.). Distribution chart 2006 may display the percentage of tasks (e.g., determined by time spent doing tasks and/or the total number of tasks assigned to and carried out by the caregiver) that each caregiver handles for the user.

Charts 2002, 2004, and 2006 may assist the user and/or caregivers in determining if the assigning of tasks is fair and if one or more caregivers are not contributing sufficiently to the care team. Activity trends page 2000 may further include a "Back" button 2008 that, when clicked, causes the application to display user's care activities page 1900.

In other embodiments, the application may include additional features and functionality. For example, the application may present a user interface to the user and/or caregivers including an option for the user and/or caregivers to view or input additional data to their profile. The application may additionally provide an option for the user and/or caregivers to input, view, and/or edit medication information for the user. For example, the user and/or caregivers may be able to see the user's daily medication schedule and determine if the user is taking the medication (e.g., through a sensor, as described above).

Exemplary Care Coordination Support Platform

In one aspect, a care coordination support platform computer system including at least one processor in communication with at least one memory device may coordinate care. The processor may be programmed to: (i) register a user through an application, wherein the user inputs personal and scheduling data into the application, (ii) register a caregiver associated with the user through the application, wherein the caregiver inputs personal and scheduling data into the application, and wherein the caregiver is one caregiver out of a plurality of caregivers associated with the user, (iii) receive input from at least one of the user and the caregiver defining at least one event associated with the user, wherein the event includes at least one of a task, an activity, and an appointment, (iv) assign the at least one event to at least one caregiver of the plurality of caregivers based upon the personal and scheduling data of the plurality of caregivers, (v) create a care schedule of the user, wherein the care schedule of the user includes the at least one assigned event, and/or (vi) display, via the application, the care schedule to the at least one caregiver on at least one device associated with the at least one caregiver.

The care coordination support platform may further include a chatbot in communication with the at least one processor, and the processor may be programmed to: (i) receive, via the chatbot, a question regarding the at least one event from at least one of the user and the caregiver, wherein the question is at least one of a natural-language typed question and a natural-language voice question, (ii) convert, via the chatbot, the question into a query, (iii) run, via the chatbot, the query against an event database stored in the at least one memory device, (iv) transmit, via the chatbot, a response to the question to the processor, wherein the response includes an answer to the question, in response to the query returning the at least one event, (v) receive, via the chatbot, input from at least one of the user and the caregiver defining a second event associated with the user, wherein the input is at least one of a natural-language typed questions and a natural-language voice question, and/or (vi) add the second event to the care schedule of the user.

The processor may further be programmed to: (i) receive sensor data from sensors associated with at least one of the user and the caregiver, wherein the sensors include at least one of mobile device sensors, vehicle telematics sensors, home telematics sensors, and smart home device sensors, (ii)

determine, based upon the received sensor data, whether the at least one assigned event has been carried out by the respective caregiver of the plurality of caregivers, and/or (iii) notify the at least one caregiver of the plurality of caregivers whether the at least one assigned event has been carried out by the respective caregiver of the plurality of caregivers.

The processor may further be programmed to: (i) update, via the application, a calendar of the respective caregiver of the plurality of caregivers in response to the at least one event being assigned to the caregiver and/or (ii) display, via the application and based upon the calendar, a daily schedule including the at least one event assigned to the respective caregiver for each particular day.

The processor may further be programmed to: (i) determine whether the at least one event is critical to the user, (ii) receive alert preferences from the user and the caregiver, wherein the alert preferences include at least one of a preferred method of receiving an alert, whether the user and the caregiver prefer to receive alerts for all of the at least one event, whether the user and the caregiver prefer to receive alerts only for critical ones of the at least one event, and how often the user and the caregiver prefer to be alerted, (iii) transmit alerts to the user and the caregiver based upon the respective alert preferences of the user and the caregiver, (iv) monitor an active time during which each caregiver of the plurality of caregivers cares for the user, (v) store the monitored active time for each caregiver, (vi) compare the active time for each caregiver with the active time for each other caregiver, (vii) display the compared active time to each caregiver of the plurality of caregivers, wherein the compared active time is displayed for a time interval, and wherein the time interval is at least one of a week, two weeks, three weeks, a month, and a year, (viii) provide rewards for each caregiver of the plurality of caregivers based upon the active time that each caregiver cares for the user, wherein the rewards include at least one of virtual badges, virtual tokens, virtual stickers, and monetary awards, (ix) receive medication data associated with the user from one or more of the user and the caregiver, (x) provide, via the application, a daily medication list, and/or (xi) allow, via the application, the one or more of the user and the caregiver to indicate when the user takes each medication from the daily medication list.

The personal and scheduling data of the user may include user data including a name, a birthdate, a height, and a weight, user tasks including taking medicine, bathing, eating, paying bills, getting groceries, car maintenance, and home maintenance, user activities including social activities and physical activities, and user appointments including recurring appointments. The personal and scheduling data of the caregiver may include caregiver data including a name, a relationship to the user, a role in the caring of the user, and caregiver schedule information including known work and activity schedules.

The foregoing CCSP computer systems may include additional, less, or alternate functionality, including that discussed elsewhere herein. For instance, to coordinate care, the at least one processor may be configured to: input user and caregiver data into a machine learning algorithm, model, or program trained to coordinate care based upon user and caregiver data.

Exemplary Schedule Conflict Resolution

FIG. 21 illustrates an exemplary computer-implemented method for coordinating care and resolving schedule conflicts via a care coordination support platform ("CCSP") computer system 2100. The CCSP computer system may include at least one processor and/or associated transceiver in communication with at least one memory device.

The computer-implemented method 2100 may include, via one or more processors and/or associated transceivers, building, creating, and/or otherwise generating 2102 an electronic calendar for a senior with multiple tasks, appointments, and/or activities (or "events," as used herein), with multiple caregivers (etc., professional caregivers, service providers, medical offices, family members, friends, etc.) having electronic access to the calendar. The generating 2102 of the senior's calendar may include the registering user and caregiver functionality; defining event (such as tasks, appointments, and/or activities, as discussed herein) functionality; and/or assigning event functionality as discussed elsewhere herein.

The computer-implemented method 2100 may include, via one or more processors and/or associated transceivers, collecting 2104 updated schedule information, mobile device data, sensor data (such as wearable sensor data, smart home sensor data, and/or smart vehicle sensor data), social media data, and/or other schedule-related data associated with the multiple caregivers having access to the electronic calendar and/or the senior.

The computer-implemented method 2100 may include, via one or more processors and/or associated transceivers, analyzing 2106 the updated schedule-related data to determine whether any schedule conflicts exist. For instance, the method 2100 may include, via one or more processors and/or associated transceivers, inputting the updated schedule-related data into a machine learning algorithm, model, module, or program trained to identify schedule or calendar conflicts based upon calendar and/or schedule-related data associated with a senior and multiple caregivers and/or service providers.

When a schedule conflict is identified, the computer-implemented method 2100 may include, via one or more processors and/or associated transceivers, analyzing 2108 the schedule-related data to determine a resolution to the schedule conflict. For instance, the method 2100 may include, via one or more processors and/or associated transceivers, inputting the updated schedule-related data into a machine learning program, model, module, or algorithm trained to determine calendar conflict resolutions using updated schedule-related data associated with the senior and/or multiple caregivers or service providers.

The computer-implemented method 2100 may include, via one or more processors and/or associated transceivers, invoking 2110 a calendar chatbot to orally or verbally explain the schedule conflict to the senior and/or caregivers, and orally or verbally propose the scheduling conflict resolution identified.

The computer-implemented method 2100 may include, via one or more processors and/or associated transceivers, receiving 2112 acceptance or acknowledgement of the scheduling change/conflict resolution from the senior and/or caregivers, such as via wireless communication or data transmission with the mobile devices, or other computing devices, of the senior and/or caregivers.

Additionally or alternatively, when a schedule conflict is identified, the computer-implemented method 2100 may include, via one or more processors and/or associated transceivers, invoking 2114 the calendar chatbot to orally or verbally engage the senior and/or one or more caregivers, such as via their mobile or other computing devices, to explain the schedule conflict.

The computer-implemented method 2100 may then include, via one or more processors and/or associated transceivers, engaging 2116 in a conversation with the senior and/or one or more caregivers via the calendar chatbot to arrive at a calendar conflict resolution. For instance, the one or more processors may analyze the updated schedule-related data to identify potential replacement caregivers for a scheduled appointment or activity, or to identify potential replacement times for a given appointment or activity with a specific caregiver. Additionally or alternatively, the calendar chatbot may ask the senior and/or a caregiver for one or more replacement times and/or alternate caregivers for an event (e.g., task, activity, or appointment) that has to be rescheduled.

After which, the computer-implemented method 2100 may include, via one or more processors and/or associated transceivers, updating 2118 the senior's calendar, and transmitting electronic notifications of the scheduling/calendar change to the mobile or other computing devices of the senior and/or caregivers. The computer-implemented method 2100 may include additional, less, or alternate actions, including those discussed elsewhere herein.

In one aspect, a care coordination support platform ("CCSP") computer system for coordinating care may be provided. The CCSP computer system may include at least one processor and/or associated transceiver in communication with at least one memory device. The at least one processor and/or associated transceiver may be programmed to: (1) register a senior (or other user) through an application, wherein the senior inputs personal and scheduling data into the application; (2) register multiple caregivers associated with the senior through the application, wherein each caregiver inputs personal and scheduling data into the application; (3) receive input from at least one of the senior and the caregiver defining at least one event associated with the senior, wherein the event includes at least one of a task, an activity, and an appointment; (4) assign the at least one event to at least one caregiver of the multiple caregivers based upon the personal and scheduling data of the multiple caregivers; (5) create a care schedule of the senior, wherein the care schedule of the senior includes the at least one assigned event; (6) receive updated scheduling-related data associated with the senior and/or the multiple caregivers; and/or (7) compare the care schedule of the senior with the updated scheduling-related data to determine a calendar conflict associated with the senior and/or at least one caregiver. The CCSP computer system may include additional, less, or alternate functionality, including that discussed elsewhere herein.

For instance, the at least one processor and/or associated transceiver may be further configured to invoke a chatbot to verbally explain to the senior or a caregiver that a calendar conflict exists. The at least one processor and/or associated transceiver may be further configured to analyze the care schedule of the senior with the updated scheduling-related data to determine an alternate caregiver that is available at the time and date of the calendar conflict to resolve the calendar conflict. The at least one processor and/or associated transceiver may be further configured to invoke a chatbot to verbally explain to the senior or a caregiver that a calendar conflict exists, and verbally explain a resolution to the calendar conflict involving the alternate caregiver.

The at least one processor and/or associated transceiver may be further configured to determine a resolution to the calendar conflict from processor analysis of the schedule-related data, and further configured to invoke a chatbot to verbally explain to the senior or a caregiver that a calendar conflict exists, and verbally explain the resolution to the calendar conflict determined from analysis of the schedule-related data.

The at least one processor and/or associated transceiver may be further configured to input the schedule-related data into a machine learning algorithm, model, module, or program that is trained to identify calendar or scheduling conflicts and/or associated scheduling resolutions using schedule-related and/or calendar data associated with seniors and multiple caregivers.

The at least one event may be a medical-related event or a doctor's appointment; taking a prescribed medication at a given time; an exercise or physical fitness event; a home delivery; a grocery delivery; a vehicle or home repair event; and/or other events, including those discussed elsewhere herein.

In another aspect, a computer-implemented method for coordinating care and resolving schedule conflicts may be provided. The computer-implemented method may be performed by a care coordination support platform ("CCSP") computer system including at least one processor and/or associated transceiver in communication with at least one memory device. The computer-implemented method may include (1) registering a senior (or other user) through an application, wherein the senior inputs personal and scheduling data into the application; (2) registering multiple caregivers associated with the senior through the application, wherein each caregiver inputs personal and scheduling data into the application; (3) receiving input from at least one of the senior and the caregiver defining at least one event associated with the senior, wherein the event includes at least one of a task, an activity, and an appointment; (4) assigning the at least one event to at least one caregiver of the multiple caregivers based upon the personal and scheduling data of the multiple caregivers; (5) creating a care schedule of the senior, wherein the care schedule of the senior includes the at least one assigned event; (6) receiving updated scheduling-related data associated with the senior and/or the multiple caregivers; and/or (7) comparing the care schedule of the senior with the updated scheduling-related data to determine a calendar conflict associated with the senior and/or at least one caregiver. The method may include additional, less, or alternate actions, including those discussed elsewhere herein.

For instance, the method may include invoking a chatbot to verbally explain to the senior or a caregiver that a calendar conflict exists. The method may further include analyzing the care schedule of the senior with the updated scheduling-related data to determine an alternate caregiver that is available at the time and date of the calendar conflict to resolve the calendar conflict. The method may further include invoking a chatbot to verbally explain to the senior or a caregiver that a calendar conflict exists, and/or verbally explain a resolution to the calendar conflict involving the alternate caregiver.

The method may further include determining a resolution to the calendar conflict from processor analysis of the schedule-related data, and invoking a chatbot to verbally explain to the senior or a caregiver that a calendar conflict exists, and verbally explain the resolution to the calendar conflict determined from analysis of the schedule-related data.

The method may further include inputting the schedule-related data into a machine learning algorithm, model, module, or program that is trained to identify calendar or scheduling conflicts and/or associated scheduling resolutions using schedule-related and/or calendar data associated with seniors and multiple caregivers.

In another aspect, a care coordination support platform ("CCSP") computer system for coordinating care and resolving schedule conflicts may be provided. The CCSP computer system may include at least one processor and/or associated transceiver in communication with at least one memory device. The at least one processor and/or associated transceiver may be programmed to: (1) build, create, or otherwise generate a senior calendar (for a senior or other user) (i) with tasks, appointments, and/or activities (and/or other events) and (ii) with multiple caregivers having access to the senior calendar, wherein individual caregivers are assigned responsibilities for certain tasks, appointments, and/or activities; (2) collect updated schedule information, mobile device data, sensor data (such as home, vehicle, or wearable sensor data), social medic data, and/or other updated schedule-related data associated with the multiple caregivers and/or the senior (such as via wireless communication and/or data transmission over one or more radio frequency links); and/or (3) analyze the updated schedule-related data to determine a schedule conflict to facilitate coordinating care for the senior. The CCSP computer system may include additional, less, or alternate functionality, including that discussed elsewhere herein.

For instance, the at least one processor and/or associated transceiver may be programmed to: input the schedule-related data into a machine learning algorithm, model, module, or program trained to identify schedule conflict and/or resolutions to schedule conflicts based upon schedule-related data received from a senior and multiple caregivers.

The at least one processor and/or associated transceiver may be programmed to: when a schedule conflict is identified, analyze the schedule-related data to determine a resolution to the schedule conflict. The at least one processor and/or associated transceiver may be programmed to: when a schedule conflict is identified, input the schedule-related data into a machine learning algorithm, model, module, or program trained to identify resolutions to schedule conflicts based upon schedule-related data received from a senior and multiple caregivers.

The at least one processor and/or associated transceiver may be programmed to: invoke a calendar chatbot to verbally explain the schedule conflict and/or one or more proposed resolutions to the schedule conflict to the senior and/or one or more caregivers. The at least one processor and/or associated transceiver may be programmed to: receive verbal acceptance of the proposed resolution to the schedule conflict from the senior and/or one or more caregivers (such as via a mobile device or other computing device and a caregiver application). The at least one processor and/or associated transceiver may be programmed to: update the senior's calendar with a conflict resolution accepted by the senior or a caregiver, and/or generate and transmit electronic notifications of the scheduling change to the senior's mobile device and one or more caregiver mobile devices.

The at least one processor and/or associated transceiver may be programmed to: when a schedule conflict is identified, invoke a calendar chatbot to verbally engage the senior and/or one or more caregivers to verbally explain the schedule conflict and/or engage in conversation with the senior and/or one or more caregivers via a calendar chatbot to verbally arrive at a calendar or schedule conflict resolution.

In another aspect, a computer-implemented method for coordinating care and resolving schedule conflicts may be provided. The computer-implemented method may be performed by a care coordination support platform ("CCSP") computer system including at least one processor and/or associated transceiver in communication with at least one memory device. The computer-implemented method may include (1) building, creating, or otherwise generating a senior calendar (for a senior or other user) (i) with tasks, appointments, and/or activities (and/or other events) and (ii) with multiple caregivers having access to the senior calendar, wherein individual caregivers are assigned responsibilities for certain tasks, appointments, and/or activities; (2) collecting updated schedule information, mobile device data, sensor data (such as home, vehicle, or wearable sensor data), social medic data, and/or other updated schedule-related data associated with the multiple caregivers and/or the senior (such as via wireless communication and/or data transmission over one or more radio frequency links); and/or (3) analyzing the updated schedule-related data to determine a schedule conflict to facilitate coordinating care for the senior. The method may include additional, less, or alternate actions, including those discussed elsewhere herein.

For instance, the method may include inputting the schedule-related data into a machine learning algorithm, model, module, or program trained to identify schedule conflict and/or resolutions to schedule conflicts based upon schedule-related data received from a senior and multiple caregivers.

The method may include, when a schedule conflict is identified, analyzing the schedule-related data to determine a resolution to the schedule conflict. The method may include, when a schedule conflict is identified, inputting the schedule-related data into a machine learning algorithm, model, module, or program trained to identify resolutions to schedule conflicts based upon schedule-related data received from a senior and multiple caregivers. The method may include invoking a calendar chatbot to verbally explain the schedule conflict and/or one or more proposed resolutions to the schedule conflict to the senior and/or one or more caregivers. The method may further include receiving verbal acceptance of the proposed resolution to the schedule conflict from the senior and/or one or more caregivers (such as via the senior's or caregiver's mobile device or other computing device and a care coordination application installed thereon).

The method may further include, when a schedule conflict is identified, invoking a calendar chatbot to verbally engage the senior and/or one or more caregivers to verbally explain the schedule conflict. The method may also include, when a schedule conflict is identified, engaging in conversation with the senior and/or one or more caregivers via a calendar chatbot to verbally arrive at a calendar or schedule conflict resolution. The method may further include updating the senior's calendar with a conflict resolution verbally or otherwise accepted by the senior or a caregiver, and/or generating and transmitting notifications of the scheduling change to the senior's mobile device and one or more caregiver mobile devices.

Exemplary Event Monitoring & Automatic Calendar Update

Figure 22:
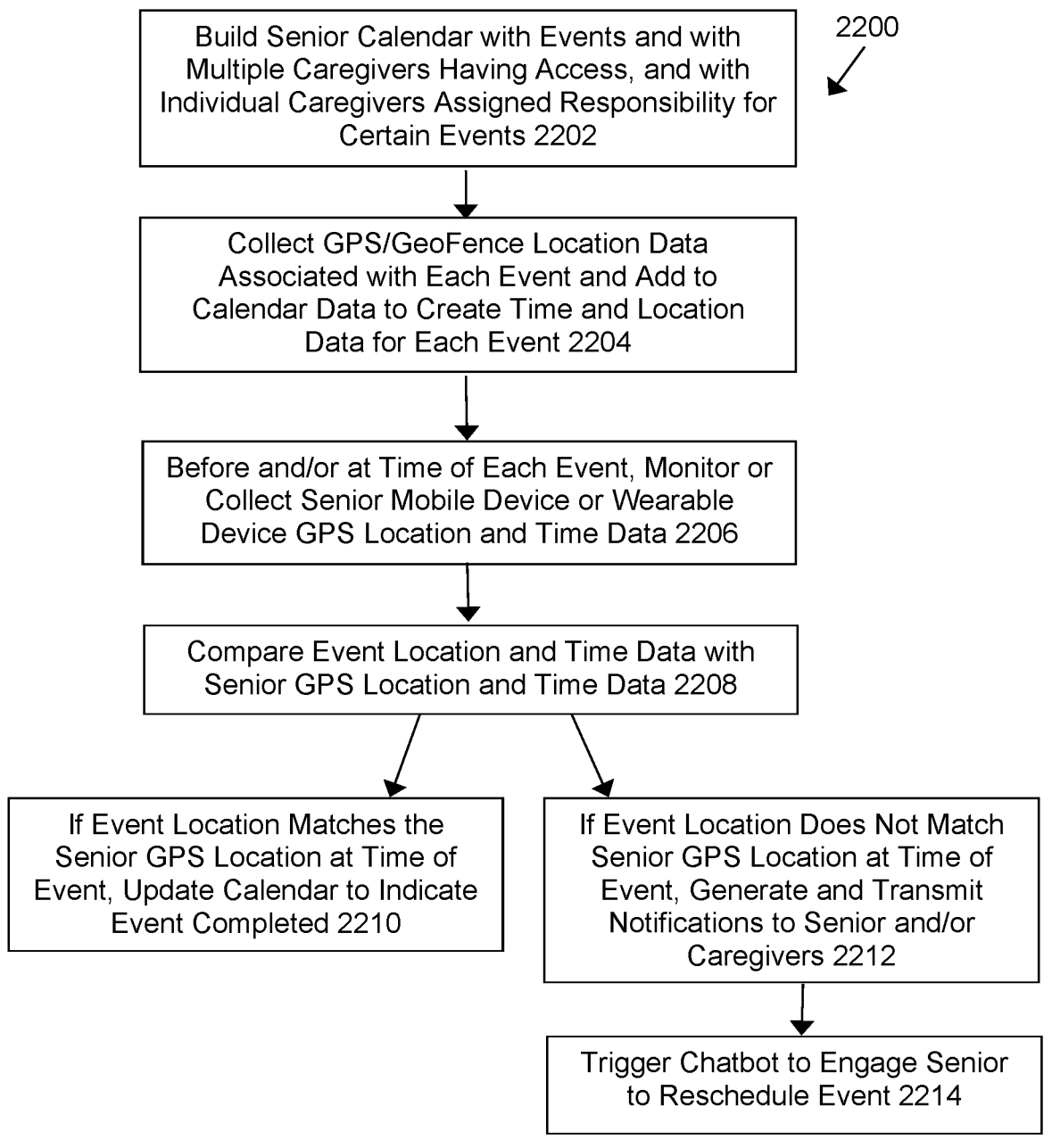
FIG. 22 illustrates an exemplary computer-implemented method for coordinating care and monitoring whether events have occurred as scheduled, or alternatively need to be rescheduled, via a care coordination support platform ("CCSP") computer system.

FIG. 22 illustrates an exemplary computer-implemented method for coordinating care and monitoring whether events have occurred as scheduled, or alternatively need to be rescheduled, via a care coordination support platform ("CCSP") computer system 2200. The CCSP computer system may include at least one processor and/or associated transceiver in communication with at least one memory device.

The computer-implemented method 2200 may include, via one or more processors and/or associated transceivers, building, creating, and/or otherwise generating 2202 an electronic calendar for a senior with multiple events (such as tasks, appointments, and/or activities, etc.), and with multiple caregivers (professional caregivers, service providers, medical offices, family members, friends, etc.) having electronic access to the calendar. The generating 2202 of the senior calendar may include the registering user and caregiver functionality; defining event (e.g., task, appointment, and/or activity) functionality; and/or assigning event functionality as discussed elsewhere herein.

The computer-implemented method 2200 may include, via one or more processors and/or associated transceivers, collecting 2204 GPS (Global Positioning System) and/or geofence location data associated with each event (e.g., task, appointment, and/or activity), and then add the GPS and geofence location data to the calendar data to create time and location data for each event (i.e., create event time and location data for each event).

Before and/or at the time of each event, the computer-implemented method 2200 may include, via one or more processors and/or associated transceivers, monitoring and/or collecting 2206 senior mobile device or wearable device GPS location and time data. For instance, the one or more processors and/or associated transceivers may query the mobile device, wearable device, or other computing devices associated with the senior (such as a smart home controller or smart vehicle computing device) to receive or otherwise determine the current GPS location of the senior.

The computer-implemented method 2200 may include, via one or more processors and/or associated transceivers, comparing 2208 the event location and time data with the senior's GPS location and time data to facilitate determining whether the event took place as scheduled, or if the event did not occur as scheduled, and needs to be rescheduled.

If the event location matches the senior's GPS location before and/or at the time of the event, the computer-implemented method 2200 may include, via one or more processors and/or associated transceivers, updating 2210 the electronic calendar of the senior to indicate that the event (task, activity, appointment, etc.) has been completed. After which, an electronic notification indicating event completion may be transmitted to the mobile devices or other computing devices of one or more caregivers and/or the senior.

If the event location does not match the senior's GPS location before and/or at the time of the event, the computer-implemented method 2200 may include, via one or more processors and/or associated transceivers, generating and transmitting 2212 electronic notifications indicating that the event did not occur as scheduled, and/or that the event needs to be rescheduled, to the mobile devices or other computing devices of the senior and/or one or more caregivers. The computer-implemented method 2200 may then include, via one or more processors and/or associated transceivers, triggering 2214 the chat to engage the senior and/or one or more caregivers to reschedule the event.

In some embodiments, the computer system and method may classify each event as being either critical or non-critical events. For instance, taking prescribed medications at the prescribed time, and/or attending medical appointments may be deemed to be critical events that should be rescheduled if they are not completed as originally scheduled. Other events, such as attending a playing or seeing a movie may be deemed non-critical, and may or may not need to be rescheduled.

In some embodiments, the one or more processors may analyze updated schedule-related information of the senior and/or caregivers to identify potential replacement times for the event, and the chatbot may then verbally propose one or more replacement times and/or locations to the senior. Additionally or alternatively, the chatbot may verbally engage the senior and/or caregiver, and ask for one or more replacement times and/or locations for the event. The method 2200 may include additional, less, or alternate actions, including those discussed elsewhere herein.

In one aspect, a care coordination support platform ("CCSP") computer system for coordinating care and monitoring whether scheduled calendar events have or have not occurred as scheduled may be provided. The CCSP computer system may include at least one processor and/or associated transceiver in communication with at least one memory device. The at least one processor and/or associated transceiver may be programmed to: (1) build, create, or otherwise generate a senior calendar (for a senior or other user) (i) with events (such as tasks, appointments, and/or activities) and (ii) with multiple caregivers having access to the senior calendar, wherein individual caregivers are assigned responsibilities for certain tasks, appointments, and/or activities; (2) collect GPS (Global Positioning System) and/or geofence location data associated with each scheduled event; (3) add the location data associated with each event to calendar (or time) data to create time and location data for each event; (4) before and/or at the time of each event, monitor and/or collect senior GPS location and time data defining a location of the senior at a specific time, the senior GPS location data originating from a mobile device, wearable, vehicle controller, smart home controller, or other computing device associated with the senior; and/or (5) compare the event location and time data with the senior GPS location and time data to facilitate monitoring event completion and care coordination. The CCSP computer system may include additional, less, or alternate functionality, including that discussed elsewhere herein.

For instance, the at least one processor and/or associated transceiver may be programmed to: if the event location and time data matches the senior GPS location and time data, update the electronic calendar of the senior to indicate that the event was completed.

The at least one processor and/or associated transceiver may be programmed to: if the event location and time data does not match the senior GPS location and time data, update the electronic calendar of the senior to indicate that the event was not completed, and/or generate and transmit an electronic notification to the mobile device or other computing device of the senior and/or one or more caregivers indicating that the event was not completed as scheduled.

The at least one processor and/or associated transceiver may be programmed to: if the event location and time data does not match the senior GPS location and time data, trigger or invoke a calendar chatbot to verbally engage the senior and/or one or more caregivers in conversation to reschedule the event or otherwise resolve an uncompleted event.

In another aspect, a computer-implemented method for coordinating care and monitoring whether scheduled calendar events have or have not occurred as scheduled. The computer-implemented method may be performed by a care coordination support platform ("CCSP") computer system including at least one processor and/or associated transceiver in communication with at least one memory device. The computer-implemented method may include (1) building, creating, or generating a senior calendar (for a senior or other user) (i) with events (such as tasks, appointments, and/or activities) and (ii) with multiple caregivers having access to the senior calendar, wherein individual caregivers are assigned responsibilities for certain tasks, appointments, and/or activities; (2) collecting GPS (Global Positioning System) and/or geofence location data associated with each scheduled event; (3) adding the location data associated with each event to calendar (or time) data to create time and location data for each event; (4) before and/or at the time of each event, monitoring and/or collecting senior GPS location and time data defining a location of the senior at a specific time, the senior GPS location data originating from a mobile device, wearable, vehicle controller, smart home controller, or other computing device associated with the senior; and/or (5) comparing the event location and time data with the senior GPS location and time data to facilitate monitoring event completion and care coordination.

The method may include, if the event location and time data matches the senior GPS location and time data, updating the electronic calendar of the senior to indicate that the event was completed. The method may include, if the event location and time data does not match the senior GPS location and time data, updating the electronic calendar of the senior to indicate that the event was not completed, and/or generating and transmitting an electronic notification to the mobile device or other computing device of the senior and/or one or more caregivers indicating that the event was not completed.

The method may include, if the event location and time data does not match the senior GPS location and time data, triggering or invoking a calendar chatbot to verbally engage the senior and/or one or more caregivers in conversation to reschedule the event or otherwise resolve an uncompleted event.

Machine Learning & Other Matters

The computer systems and computer-implemented methods discussed herein may include additional, less, or alternate actions and/or functionalities, including those discussed elsewhere herein. The computer systems may include or be implemented via computer-executable instructions stored on non-transitory computer-readable media. The methods may be implemented via one or more local or remote processors, transceivers, servers, and/or sensors (such as processors, transceivers, servers, and/or sensors mounted on mobile computing devices, or associated with smart infrastructure or remote servers), and/or via computer executable instructions stored on non-transitory computer-readable media or medium.

In some embodiments, a care coordination support platform computing device is configured to implement machine learning, such that the care coordination support platform computing device "learns" to analyze, organize, and/or process data without being explicitly programmed. Machine learning may be implemented through machine learning methods and algorithms ("ML methods and algorithms"). In an exemplary embodiment, a machine learning module ("ML module") is configured to implement ML methods and algorithms. In some embodiments, ML methods and algorithms are applied to data inputs and generate machine learning outputs ("ML outputs"). Data inputs may include but are not limited to: user data, caregiver data, sensor data, assignment data, calendar data, task data, and/or alert data. ML outputs may include but are not limited to: user data, caregiver data, calendar data, task data, and/or assignment data. In some embodiments, data inputs may include certain ML outputs.

In some embodiments, at least one of a plurality of ML methods and algorithms may be applied, which may include but are not limited to: linear or logistic regression, instance-based algorithms, regularization algorithms, decision trees, Bayesian networks, cluster analysis, association rule learning, artificial neural networks, deep learning, combined learning, reinforced learning, dimensionality reduction, and support vector machines. In various embodiments, the implemented ML methods and algorithms are directed toward at least one of a plurality of categorizations of machine learning, such as supervised learning, unsupervised learning, and reinforcement learning.

In one embodiment, the ML module employs supervised learning, which involves identifying patterns in existing data to make predictions about subsequently received data. Specifically, the ML module is "trained" using training data, which includes example inputs and associated example outputs. Based upon the training data, the ML module may generate a predictive function which maps outputs to inputs and may utilize the predictive function to generate ML outputs based upon data inputs. The example inputs and example outputs of the training data may include any of the data inputs or ML outputs described above. For example, a ML module may receive training data comprising user data, caregiver data, and assignment data associated with the user data and caregiver data. The ML module may then generate a model which maps assignment data to aspects of user data and caregiver data. The ML module may then generate assignment data as a ML output based upon subsequently received user data and caregiver data.

In another embodiment, a ML module may employ unsupervised learning, which involves finding meaningful relationships in unorganized data. Unlike supervised learning, unsupervised learning does not involve user-initiated training based upon example inputs with associated outputs. Rather, in unsupervised learning, the ML module may organize unlabeled data according to a relationship determined by at least one ML method/algorithm employed by the ML module. Unorganized data may include any combination of data inputs and/or ML outputs as described above. For example, a ML module may receive unlabeled data comprising user data, caregiver data, and calendar data. The ML module may employ an unsupervised learning method such as "clustering" to identify patterns and organize the unlabeled data into meaningful groups. The newly organized data may be used, for example, to generate a model which associates user data and caregiver data to calendar data.

In yet another embodiment, a ML module may employ reinforcement learning, which involves optimizing outputs based upon feedback from a reward signal. Specifically, the ML module may receive a user-defined reward signal definition, receive a data input, utilize a decision-making model to generate a ML output based upon the data input, receive a reward signal based upon the reward signal definition and the ML output, and alter the decision-making model so as to receive a stronger reward signal for subsequently generated ML outputs. Other types of machine learning may also be employed, including deep or combined learning techniques.

The reward signal definition may be based upon any of the data inputs or ML outputs described above. For example, a ML module may implement reinforcement learning in generating assignment data for caregivers. The ML module may utilize a decision-making model to generate assignment data for caregivers based upon task data, and may further receive user-satisfaction data indicating a level of satisfaction experienced by a user and a caregiver who engaged in a transaction (e.g., the caregiver carrying out a task for the user). A reward signal may be generated by comparing the user-satisfaction data to an assignment score between the user and the caregiver.

Based upon the reward signal, the ML module may update the decision-making model such that subsequently generated assignment scores more accurately predict user satisfaction. For example, the ML module may determine that a specific caregiver has taken the user to four doctor's appointments. The user may enjoy the caregiver taking the user to the doctor's appointments, and the caregiver may enjoy taking the user to the doctor's appointments because the doctor's appointments may be close to the caregiver's house. Therefore, the user and the caregiver may both rate the "transaction" highly. Accordingly, the ML module may learn to automatically assign doctor's appointments to the specific caregiver.

ADDITIONAL CONSIDERATIONS

With the foregoing, users and caregivers may opt-in or register to a care coordination support platform program or other type of program. After the users and caregivers give their affirmative consent or permission, a care coordination support platform remote server may collect data from the mobile devices, user computing devices, smart home controllers, smart vehicles, autonomous or semi-autonomous vehicles, smart infrastructure, smart buildings, smart aerial devices (e.g., drones), and/or other smart devices, such as with the permission or affirmative consent of the users and caregivers. The data collected may be related to user activities and/or user/caregiver schedules and current locations.

As will be appreciated based upon the foregoing specification, the above-described embodiments of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed embodiments of the disclosure. The computer-readable media may be, for example, but is not limited to, a fixed (hard) drive, diskette, optical disk, magnetic tape, semiconductor memory such as read-only memory (ROM), and/or any transmitting/receiving medium such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one embodiment, a computer program is provided, and the program is embodied on a computer readable medium. In an exemplary embodiment, the system is executed on a single computer system, without requiring a connection to a sever computer. In a further embodiment, the system is being run in a Windows® environment (Windows is a registered trademark of Microsoft Corporation, Redmond, Washington). In yet another embodiment, the system is run on a mainframe environment and a UNIX® server environment (UNIX is a registered trademark of X/Open Company Limited located in Reading, Berkshire, United Kingdom). The application is flexible and designed to run in various different environments without compromising any major functionality. In some embodiments, the system includes multiple components distributed among a plurality of computing devices. One or more components may be in the form of computer-executable instructions embodied in a computer-readable medium. The systems and processes are not limited to the specific embodiments described herein. In addition, components of each system and each process can be practiced independent and separate from other components and processes described herein. Each component and process can also be used in combination with other assembly packages and processes.

In some embodiments, registration of users for the care coordination support platform includes opt-in informed consent of users to data usage by the smart home devices, wearable devices, mobile devices, autonomous vehicles, and/or smart vehicles consistent with consumer protection laws and privacy regulations. In some embodiments, the user data, the caregiver data, and/or other collected data may be anonymized and/or aggregated prior to receipt such that no personally identifiable information (PII) is received. In other embodiments, the system may be configured to receive user and caregiver data and/or other collected data that is not yet anonymized and/or aggregated, and thus may be configured to anonymize and aggregate the data. In such embodiments, any PII received by the system is received and processed in an encrypted format, or is received with the consent of the individual with which the PII is associated. In situations in which the systems discussed herein collect personal information about individuals, or may make use of such personal information, the individuals may be provided with an opportunity to control whether such information is collected or to control whether and/or how such information is used. In addition, certain data may be processed in one or more ways before it is stored or used, so that personally identifiable information is removed.

As used herein, an element or step recited in the singular and proceeded with the word "a" or "an" should be understood as not excluding plural elements or steps, unless such exclusion is explicitly recited. Furthermore, references to "exemplary embodiment" or "one embodiment" of the present disclosure are not intended to be interpreted as excluding the existence of additional embodiments that also incorporate the recited features.

The patent claims at the end of this document are not intended to be construed under 35 U.S.C. § 112(f) unless traditional means-plus-function language is expressly recited, such as "means for" or "step for" language being expressly recited in the claim(s).

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A care coordination support platform ("CCSP") computer system for coordinating care, the CCSP computer system including at least one processor and/or associated transceiver in communication with at least one memory device, the at least one processor and/or associated transceiver are programmed to:

receive input from a senior user defining a first event associated with the senior user, wherein the first event is at a first time and includes at least one of a task, an activity, or an appointment;

create a care schedule of the senior user, wherein the care schedule of the senior user includes a plurality of events including the first event, and wherein the first event is assigned to a service provider;

identify a calendar conflict associated with the senior user and the service provider based upon comparing the care schedule of the senior user at the first time with scheduling data of the service provider at the first time;

generate and transmit a notification of the calendar conflict to a user device associated with the senior user;

receive, via a chatbot, a question regarding the first event and the calendar conflict from the senior user, wherein the question is a natural-language voice question;

convert, via the chatbot, the question into a query;

run, via the chatbot, the query against an event database stored in the at least one memory device;

generate, via the chatbot, a response to the question in natural language, the response comprising a recommendation to resolve the calendar conflict associated with the senior user and the service provider based upon the query run against the event database, the recommendation comprising rescheduling the first event with the service provider at a second time or with a different service provider at the first time;

instruct the user device associated with the senior user to audibly present the response to the senior user.

2. The CCSP computer system of claim 1, wherein the at least one processor and/or associated transceiver is further configured to:

receive, via the chatbot, another input from the senior user defining a second event associated with the senior user, wherein the another input is a second natural-language voice question;

assign a second service provider to the second event; and add the second event to the care schedule of the senior user based on the input.

3. The CCSP computer system of claim 1, wherein the at least one processor and/or associated transceiver is further configured to:

generate, via the chatbot, an audio alert of the calendar conflict, wherein the audio alert is in natural language and describes the calendar conflict including identifying the service provider assigned to the first event; and instruct a computing device associated with one of the senior user or the service provider to audibly present the audio alert to at least one of the senior user or the service provider.

4. The CCSP computer system of claim 1, wherein the at least one processor and/or associated transceiver is further configured to invoke the chatbot to explain to both the senior user and the service provider that the calendar conflict exists.

5. The CCSP computer system of claim 1, wherein the at least one processor and/or associated transceiver is further configured to analyze the care schedule of the senior user with the scheduling data to determine that the different service provider is available at the first time to resolve the calendar conflict.

6. The CCSP computer system of claim 5, wherein the at least one processor and/or associated transceiver is further configured to invoke the chatbot to verbally explain to the senior user or the service provider that the calendar conflict exists, and verbally explain the recommendation involving the different service provider.

7. The CCSP computer system of claim 1, wherein the at least one processor and/or associated transceiver is further configured to input schedule-related data into a machine learning algorithm, model, module, or program that is trained to identify calendar or scheduling conflicts and/or associated scheduling resolutions using schedule-related and/or calendar data associated with seniors and multiple caregivers.

8. The CCSP computer system of claim 1, wherein the first event is a medical-related event or a doctor's appointment.

9. The CCSP computer system of claim 1, wherein the first event is an exercise or physical fitness event.

10. The CCSP computer system of claim 1, wherein the first event is a vehicle or home repair event.

11. A computer-implemented method for coordinating care, the computer-implemented method performed by a care coordination support platform ("CCSP") computer system including at least one processor in communication with at least one chatbot and at least one memory device, the computer-implemented method comprising:

receiving input from a senior user defining a first event associated with the senior user, wherein the first event is at a first time and includes at least one of a task, an activity, or an appointment;

creating a care schedule of the senior user, wherein the care schedule of the senior user includes a plurality of events including the first event, and wherein the first event is assigned to a service provider;

identifying a calendar conflict associated with the senior user and the service provider based upon comparing the care schedule of the senior user at the first time with scheduling data of the service provider at the first time;

generating and transmitting a notification of the calendar conflict to a user device associated with the senior user;

receiving, via the at least one chatbot, a question regarding the first event and the calendar conflict from the senior user, wherein the question is a natural-language voice question;

converting, via the at least one chatbot, the question into a query;

running, via the at least one chatbot, the query against an event database stored in the at least one memory device;

generating, via the at least one chatbot, a response to the question in natural language, the response comprising a recommendation to resolve the calendar conflict associated with the senior user and the service provider based upon the query run against the event database, the recommendation comprising rescheduling the first event with the service provider at a second time or with a different service provider at the first time;

instructing the user device associated with the senior user to audibly present the response to the senior user.

12. The computer-implemented method of claim 11 further comprising:

receiving, via the at least one chatbot, another input from the senior user defining a second event associated with the senior user, wherein the another input is a second natural-language voice question;

assigning a second service provider to the second event; and adding the second event to the care schedule of the senior user based on the input.

13. The computer-implemented method of claim 11 further comprising:

generating, via the at least one chatbot, an audio alert of the calendar conflict, wherein the audio alert is in natural language and describes the calendar conflict including identifying the service provider assigned to the first event; and instructing a computing device associated with one of the senior user or the service provider to audibly present the audio alert to at least one of the senior user or the service provider.

14. The computer-implemented method of claim 11 further comprising invoking the at least one chatbot to explain to both the senior user and the service provider that the calendar conflict exists.

15. The computer-implemented method of claim 11 further comprising analyzing the care schedule of the senior user with the scheduling data to determine that the different service provider is available at the first time to resolve the calendar conflict.

16. The computer-implemented method of claim 15 further comprising invoking the at least one chatbot to verbally explain to the senior user or the service provider that the calendar conflict exists, and verbally explain the recommendation involving the different service provider.

17. The computer-implemented method of claim 11 further comprising inputting schedule-related data into a machine learning algorithm, model, module, or program that is trained to identify calendar or scheduling conflicts and/or associated scheduling resolutions using schedule-related and/or calendar data associated with seniors and multiple caregivers.

18. The computer-implemented method of claim 11, wherein the first event is a medical-related event or a doctor's appointment.

19. The computer-implemented method of claim 11, wherein the first event is an exercise or physical fitness event.

20. The computer-implemented method of claim 11, wherein the first event is a vehicle or home repair event.

21. A care coordination support platform ("CCSP") computer system for coordinating care, the CCSP computer system including at least one processor and/or associated transceiver in communication with at least one memory device, the at least one processor and/or associated transceiver are programmed to:

receive input from a senior defining a first event associated with the senior, wherein the first event is at a first time and includes at least one of a task, an activity, or an appointment;

create a care schedule of the senior, wherein the care schedule of the senior includes a plurality of events including the first event, wherein the first event is assigned to a first service provider, and wherein the care schedule includes identifying service providers of a plurality of service providers assigned to the plurality of events;

receive updated scheduling-related data associated with at least one of the senior or the plurality of service providers;

identify a calendar conflict associated with the senior and the service provider based upon comparing the care schedule of the senior at the first time with the updated scheduling-related data at the first time;

generate, via a chatbot, an audio alert associated with the calendar conflict, wherein the audio alert is in natural language and describes the calendar conflict including a recommendation to resolve the calendar conflict and identifying the first service provider assigned to the first event, the recommendation comprising rescheduling the first event with the service provider at a second time or with a different service provider at the first time; and instruct a user device associated with one of the senior and the first service provider to audibly present the audio alert to the at least one of the senior and the first service provider.

* * * * *